(12) United States Patent
Choi et al.

(10) Patent No.: US 9,150,630 B2
(45) Date of Patent: Oct. 6, 2015

(54) USE OF IDBF

(75) Inventors: Kang-Yell Choi, Seoul (KR); Hyun-Yi Kim, Seoul (KR); Ju-Yong Yoon, Seoul (KR)

(73) Assignee: Industry-Academic Cooperation Foundation, Yonsei University (KR)

(*) Notice: Subject to any disclaimer, the term of this patent is extended or adjusted under 35 U.S.C. 154(b) by 105 days.

(21) Appl. No.: 13/057,473
(22) PCT Filed: Aug. 3, 2009
(86) PCT No.: PCT/KR2009/004338
§ 371 (c)(1),
(2), (4) Date: Feb. 3, 2011
(87) PCT Pub. No.: WO2010/016706
PCT Pub. Date: Feb. 11, 2010

(65) Prior Publication Data
US 2011/0135652 A1 Jun. 9, 2011

(30) Foreign Application Priority Data
Aug. 4, 2008 (KR) .................. 10-2008-0076128

(51) Int. Cl.
| A61K 38/10 | (2006.01) |
| A61K 38/17 | (2006.01) |
| C07K 7/08 | (2006.01) |
| C07K 14/435 | (2006.01) |
| C07K 19/00 | (2006.01) |
| C07K 14/47 | (2006.01) |
| A61K 47/48 | (2006.01) |

(52) U.S. Cl.
CPC ............ C07K 14/4703 (2013.01); A61K 38/10 (2013.01); A61K 38/1709 (2013.01); C07K 7/08 (2013.01); A61K 47/48246 (2013.01); A61K 47/48315 (2013.01); C07K 2319/10 (2013.01)

(58) Field of Classification Search
None
See application file for complete search history.

(56) References Cited

U.S. PATENT DOCUMENTS

2003/0104622 A1* 6/2003 Robbins et al. ............... 435/455
2009/0047276 A1* 2/2009 Moon et al. ................. 424/130.1

FOREIGN PATENT DOCUMENTS

WO WO 03/025148 * 3/2003
WO WO 2006/107719 A2 10/2006
WO WO 2007/121147 * 10/2007

OTHER PUBLICATIONS

London et al., Biochem. Biophys. Res. Commun., 2004, vol. 322:326-332.*
Seth et al., Ther. Deliv., 2012, vol. 3(2):245-261.*
Liu et al., 2014, Neurochem. Int., vol. 75:19-25.*
Akio Matsuda et al., Large-scale identification and characterization of human genes that activate Nf-kappaB and MAPK signaling pathways, Oncogene (2003) vol. 22(21), p. 3307-3318.
Andersson, T., et al. "CXXC5 Is a Novel BMP4-regulated Modulator of Wnt-Signaling in Neural Stem Cells", J. Bio Chem. vol. 284, (6) pp. 3672-3681, Nov. 10, 2008.
London, et al.,"Interaction between the internal motif KTXXXI of Idax and mDvl PDZ domain", Biochem. and Biophys. Res. Commun. vol. 322; (2004) pp. 326-332.
Michiue, T., et al., "Xtdax, an inhibitor of the canonical Wnt pathway, is required for anterior neural structure formation in Xenopus", Dev. Dyn. vol. 230, pp. 79-90, (2004).
Wong, HC., et al.,"Direct Binding of the PDZ Domain of Dishevelled to a Conserved Internal Sequence in the C-terminal Region of Frizzled", Molecular Cell, vol. 12, pp. 1251-1260, Nov. 2003.
Umbhauer, M., et al."The C-terminal cytoplasmic Lys-Thr-X-X-X-Trp motif in frizzled receptors mediated Wnt/β-catenin signalling", The EMBO Journal vol. 19, No. 18, pp. 4944-4954, 2000.
Fujii, N., et al."An Antagonist of Dishevelled Protein-Protein Interaction Suppresses β-Catenin-Dependant Tumor Cell Growth", Cancer Research vol. 67, (20), pp. 573-579, 2007.
Hino et al. (2001) Molecular and Cellular Biology 21(1):330-342 Inhibition of the Wnt Signaling Pathway by Idax, a Novel Dvl-Binding Protein.
Monroe et al. (2012) Gene 492:1-18 "Update on Wnt signaling in bone cell biology and bone disease".
Cariacasole et al., "The Wnt pathway, cell-cycle activation and beta-amyloid: novel therapeutic strategies in Alzheimer's disease?" Trends in Pharmacological Sciences, vol. 24, No. 5, pp. 233-238, May 2003.
"CXXC-type zinc finger protein 5 [Homo sapiens]" NCBI Reference Sequence: NP_057547, p. 1, May 2008.
Gong et al., "LDL Receptor-Related Protein 5 (LRP5) Affects Bone Accrual and Eye Development" Cell, vol. 107, Nov. 16, 2001, pp. 513-523.
Kondo et al., "Frizzled 4 gene (FZD4) mutations in patients with familial exudative vitreoretinopathy with variable expressivity" Br J Ophthamol, vol. 87, pp. 1291-1295, Feb. 2003.
Loughlin et al., "Functional variants within the secreted frizzled-related protein 3 gene are associated with hip osteoarthritis in females" PNAS, vol. 101, No. 26, pp. 9757-9762, Jun. 29, 2004.
Miyaoka et al., "Increased expression of Wnt-1 in schizophrenic brains" Schizophrenia Research, vol. 38, pp. 1-6, 1999.
Morin "beta-catenin signaling and cancer" BioEssays, vol. 21, pp. 1021-1030, 1999.
Polakis "The oncogenic activation of beta-catenin" Current Opinion in Genetics & Development, vol. 9, pp. 15-21, 1999.
Polakis "Wnt signaling and cancer" Genes Dev., vol. 14, pp. 1837-1851, 2000.

(Continued)

Primary Examiner — Xiaozhen Xie
(74) Attorney, Agent, or Firm — Swanson & Bratschun, L.L.C.

(57) ABSTRACT

There are provided Idbf (inhibitor of Dvl and bone formation) which is a novel Dvl-binding protein that binds to Dvl to inhibit signal transduction carried out through the Wnt/β-catenin signaling pathway, a gene for coding for the same, the use thereof, and the use of an inhibitor of the Idbf. The Idbf was known to be expressed by activation of the Wnt/β-catenin signaling pathway and bind to Dvl to block signal transduction carried out through the Wnt/β-catenin signaling pathway. Therefore, the Idbf can be used in development of medicines for inhibiting the signal transduction carried out through the Wnt/β-catenin signaling pathway, and an Idbf inhibitor can be used in preparation of medicines for activating the signal transduction carried out through the Wnt/β-catenin signaling pathway.

4 Claims, 25 Drawing Sheets
(13 of 25 Drawing Sheet(s) Filed in Color)

(56) References Cited

OTHER PUBLICATIONS

Shioi et al., "beta-Glycerophosphate Accelerates Calcification in Cultured Bovine Vascular Smooth Muscle Cells" Arteriosclerosis, Thrombosis, and Vascular Biology, vol. 15, No. 11, pp. 2003-2009, Nov. 1995.
van Gijn, et al., "The wnt-frizzled cascade in cardiovascular disease" Cardiovascular Research, vol. 55, pp. 16-24, 2002.
Van Wesenbeeck et al., "Six Novel Missense Mutations in the LDL Receptor-Related Protein 5 (LRP5) Gene in Different Conditions with an Increased Bone Density" Am. J. Hum. Genet., vol. 72, pp. 763-771, 2003.
Varallo et al., "Beta-catenin expression in Dupuytren's disease: potential role for cell-matrix interactions in modulating beta-catenin levels in vivo and in vitro" Oncogene, vol. 22, pp. 3680-3684, 2003.
Matsushita et al., "Protein transduction technology" J. Mol. Med., vol. 83, pp. 324-328, 2005.

\* cited by examiner

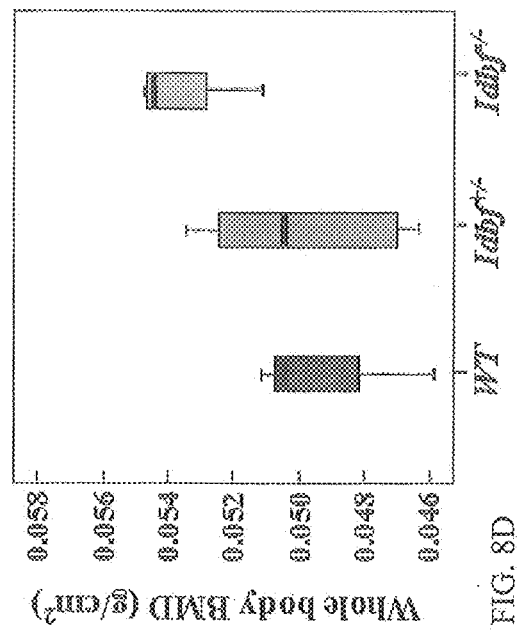
FIG. 8B
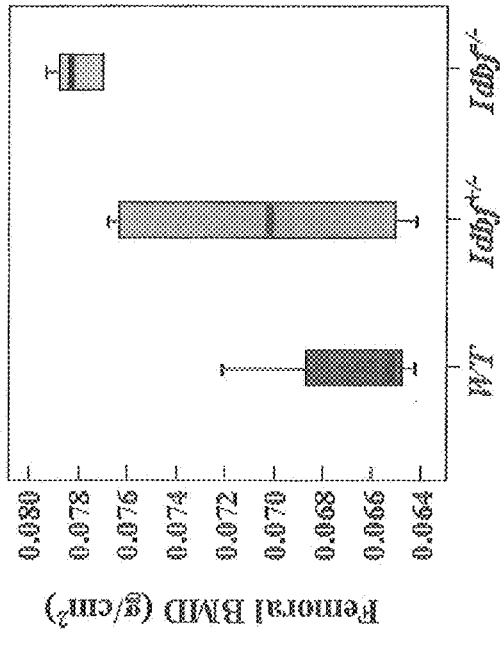
FIG. 8D
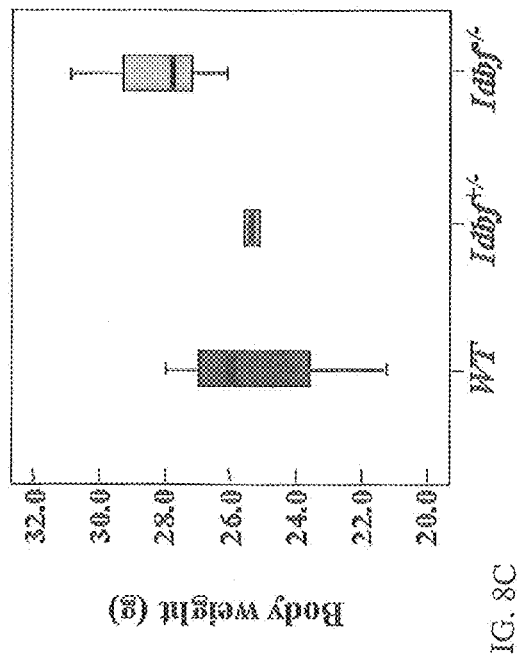
FIG. 8A
FIG. 8C

WT     *Idbf*$^{+/-}$     *Idbf*$^{-/-}$

WT     *Idbf*$^{+/-}$     *Idbf*$^{-/-}$

SEQUENCE LISTING

<160> NUMBER OF SEQ ID NOS: 29

<210> SEQ ID NO 1
<211> LENGTH: 322
<212> TYPE: PRT
<213> ORGANISM: Homo sapiens

<400> SEQUENCE: 1

```
Met Ser Ser Leu Gly Gly Gly Ser Gln Asp Ala Gly Ser Ser Ser
1               5                   10                  15

Ser Ser Thr Asn Gly Ser Gly Gly Ser Gly Ser Ser Gly Pro Lys Ala
                20                  25                  30

Gly Ala Ala Asp Lys Ser Ala Val Val Ala Ala Ala Pro Ala Ser
                35                  40                  45

Val Ala Asp Asp Thr Pro Pro Pro Glu Arg Arg Asn Lys Ser Gly Ile
    50                  55                  60

Ile Ser Glu Pro Leu Asn Lys Ser Leu Arg Arg Ser Arg Pro Leu Ser
65                  70                  75                  80

His Tyr Ser Ser Phe Gly Ser Ser Gly Gly Ser Gly Gly Gly Ser Met
                85                  90                  95

Met Gly Gly Glu Ser Ala Asp Lys Ala Thr Ala Ala Ala Ala Ala
                100                 105                 110

Ser Leu Leu Ala Asn Gly His Asp Leu Ala Ala Ala Met Ala Val Asp
                115                 120                 125

Lys Ser Asn Pro Thr Ser Lys His Lys Ser Gly Ala Val Ala Ser Leu
    130                 135                 140

Leu Ser Lys Ala Glu Arg Ala Thr Glu Leu Ala Ala Glu Gly Gln Leu
145                 150                 155                 160

Thr Leu Gln Gln Phe Ala Gln Ser Thr Glu Met Leu Lys Arg Val Val
                165                 170                 175

Gln Glu His Leu Pro Leu Met Ser Glu Ala Gly Ala Gly Leu Pro Asp
                180                 185                 190

Met Glu Ala Val Ala Gly Ala Glu Ala Leu Asn Gly Gln Ser Asp Phe
                195                 200                 205

Pro Tyr Leu Gly Ala Phe Pro Ile Asn Pro Gly Leu Phe Ile Met Thr
    210                 215                 220

Pro Ala Gly Val Phe Leu Ala Glu Ser Ala Leu His Met Ala Gly Leu
225                 230                 235                 240

Ala Glu Tyr Pro Met Gln Gly Glu Leu Ala Ser Ala Ile Ser Ser Gly
                245                 250                 255

Lys Lys Lys Arg Lys Arg Cys Gly Met Cys Ala Pro Cys Arg Arg Arg
                260                 265                 270

Ile Asn Cys Glu Gln Cys Ser Ser Cys Arg Asn Arg Lys Thr Gly His
                275                 280                 285

Gln Ile Cys Lys Phe Arg Lys Cys Glu Glu Leu Lys Lys Lys Pro Ser
    290                 295                 300

Ala Ala Leu Glu Lys Val Met Leu Pro Thr Gly Ala Ala Phe Arg Trp
305                 310                 315                 320

Phe Gln
```

<210> SEQ ID NO 2

```
<211> LENGTH: 969
<212> TYPE: DNA
<213> ORGANISM: Homo sapiens

<400> SEQUENCE: 2
atgtcgagcc tcggcggtgg ctcccaggat gccggcggca gtagcagcag cagcaccaat      60
ggcagcggtg gcagtggcag cagtggccca aaggcaggag cagcagacaa gagtgcagtg     120
gtggctgccg ccgcaccagc ctcagtggca gatgacacac cacccccga gcgtcggaac      180 aagagcggta tcatcagtga gcccctcaac aagagcctgc gccgctcccg cccgctctcc     240
cactactctt cttttggcag cagtggtggt agtggcggtg gcagcatgat gggcggagag     300
tctgctgaca aggccactgc ggctgcagcc gctgcctccc tgttggccaa tgggcatgac     360
ctggcggcgg ccatggcggt ggacaaaagc aaccctacct caaagcacaa aagtggtgct     420
gtggccagcc tgctgagcaa ggcagagcgg gccacggagc tggcagccga gggacagctg     480
acgctgcagc agtttgcgca gtccacagag atgctgaagc gcgtggtgca ggagcatctc     540
ccgctgatga gcgaggcggg tgctggcctg cctgacatgg aggctgtggc aggtgccgaa     600
gccctcaatg ccagtccga cttcccctac ctgggcgctt tccccatcaa cccaggcctc      660
ttcattatga ccccggcagg tgtgttcctg gccgagagcg cgctgcacat ggcgggcctg     720
gctgagtacc ccatgcaggg agagctggct tctgccatca gctccggcaa gaagaagcgg     780
aaacgctgcg catgtgcgc gccctgccgg cggcgcatca actgcgagca gtgcagcagt     840
tgtaggaatc gaaagactgg ccatcagatt tgcaaattca gaaatgtga ggaactcaaa      900 aagaagcctt ccgctgctct ggagaaggtg atgcttccga cgggagccgc cttccggtgg     960
tttcagtga                                                              969

<210> SEQ ID NO 3
<211> LENGTH: 1447
<212> TYPE: RNA
<213> ORGANISM: Homo sapiens

<400> SEQUENCE: 3
acugcuggcg gcuggagcgg agcgcaccgc ggcgguggug cccagagcgg agcgcagcuc      60
ccugccccgc cccucccccu cggccucgcg gcgacggcgg cgguggcggc uuggacgacu     120
cggagagccg agugaagaca uuuccaccug acaccugac caugugccug cccugagcag     180
cgaggcccac caggcaucuc uguuguggc agcagggcca gguccugguc uguggacccu     240
cggcaguugg caggcucccu cugcagugg gucuggccu cggccccacc augucgagcc      300
ucggcggugg cucccaggau gccggcggca guagcagcag cagcaccaau ggcagcggug     360
gcaguggcag caguggccca aaggcaggag cagcagacaa gagugcagug guggcugccg     420
ccgcaccagc ucagguggca gaugacacac caccccccga gcgucggaac aagagcggua     480
ucaucaguga gccccucaac aagagccugc gccgcucccg cccgcucucc cacuacucuu     540
cuuuuggcag caguggguggu aguggcggug gcagcaugau gggcggagag ucugcugaca     600
aggccacugc ggcugcagcc gcugccuccc uguuggccaa ugggcaugac cuggcggcgg     660
ccauggcggu ggacaaaagc aacccuaccu caaagcacaa aagugguguu guggccagcc     720
ugcugagcaa ggcagagcgg gccacggagc uggcagccga gggacagcug acgcugcagc     780
aguuugcgca guccacagag augcugaagc gcgguguggca ggagcaucuc ccgcugauga     840
gcgaggcggg ugcuggcug ccugacaugg aggcuggugg aggugccgaa gcccucaaug      900
gccaguccga cuucccuac cugggcgcu ucccaucaa cccaggccuc uucauuauga       960
```

```
ccccggcagg uguguuccug gccgagagcg cgcugcacau ggcgggccug gcugaguacc    1020
ccaugcaggg agagcuggcc ucugccauca gcuccggcaa gaagaagcgg aaacgcugcg    1080
gcaugugcgc gcccugccgg cggcgcauca acugcgagca gugcagcagu guaggaauc    1140 gaaagacugg ccaucagauu ugcaaauuca gaaaauguga ggaacucaaa aagaagccuu    1200
ccgcugcucu ggagaaggug augcuuccga cgggagccgc cuuccggugg uuucagugac    1260
ggcggcggaa cccaaagcug cccucuccgu gcaaugucac ugcucgugug gucuccagca    1320
agggauucgg gcgaagacaa acggaugcac ccgucuuuag aaccaaaaau auucucucac    1380
agauuucauu ccuguuuuua uauauauauu uuuguugguc guuuaacau cuccacgucc    1440 cuagcau                                                             1447
```

<210> SEQ ID NO 4
<211> LENGTH: 13
<212> TYPE: PRT
<213> ORGANISM: Homo sapiens

<400> SEQUENCE: 4

Arg Lys Thr Gly His Gln Ile Cys Lys Phe Arg Lys Cys
1               5                   10

<210> SEQ ID NO 5
<211> LENGTH: 317
<212> TYPE: PRT
<213> ORGANISM: Mus musculus

<400> SEQUENCE: 5

Met Ser Ser Leu Gly Gly Gly Ser Gln Asp Ala Gly Ser Ser Ser
1               5                   10                  15

Ser Ser Asn Thr Asn Ser Ser Gly Ser Gly Gln Lys Ala Gly Gly
                20                  25                  30

Thr Asp Lys Ser Thr Ala Val Ala Ala Thr Thr Ala Pro Thr Ser Val
                35                  40                  45

Ala Asp Asp Ala Pro Pro Glu Arg Arg Asn Lys Ser Gly Ile Ile
        50                  55                  60

Ser Glu Pro Leu Asn Lys Ser Leu Arg Arg Ser Arg Pro Leu Ser His
65              70                  75                  80

Tyr Ser Ser Phe Gly Ser Ser Gly Gly Gly Ser Met Met Gly Val
                85                  90                  95

Glu Ser Ala Asp Lys Ala Ala Ala Ala Ala Ser Leu Leu Ala Asn
                100                 105                 110

Gly His Asp Leu Ala Ala Ala Met Ala Val Asp Lys Ser Asn Pro Thr
                115                 120                 125

Ser Lys His Lys Ser Gly Ala Val Ala Ser Leu Leu Ser Lys Ala Glu
            130                 135                 140

Arg Ala Thr Glu Leu Ala Ala Glu Gly Gln Leu Thr Leu Gln Gln Phe
145                 150                 155                 160

Ala Gln Ser Thr Glu Met Leu Lys Arg Val Val Gln Glu His Leu Pro
                165                 170                 175

Leu Met Ser Glu Ala Gly Ala Gly Leu Pro Asp Met Glu Ala Val Ala
                180                 185                 190

Gly Ala Glu Ala Leu Asn Gly Gln Ser Asp Phe Pro Tyr Leu Gly Ala
            195                 200                 205

Phe Pro Ile Asn Pro Gly Leu Phe Ile Met Thr Pro Ala Gly Val Phe
        210                 215                 220

```
Leu Ala Glu Ser Ala Leu His Met Ala Gly Leu Ala Glu Tyr Pro Met
225                 230                 235                 240

Gln Gly Glu Leu Ala Ser Ala Ile Ser Ser Gly Lys Lys Lys Arg Lys
            245                 250                 255

Arg Cys Gly Met Cys Ala Pro Cys Arg Arg Arg Ile Asn Cys Glu Gln
        260                 265                 270

Cys Ser Ser Cys Arg Asn Arg Lys Thr Gly His Gln Ile Cys Lys Phe
    275                 280                 285

Arg Lys Cys Glu Glu Leu Lys Lys Lys Pro Ser Ala Ala Leu Glu Lys
290                 295                 300

Val Met Leu Pro Ser Gly Ala Ala Phe Arg Trp Phe Gln
305                 310                 315

<210> SEQ ID NO 6
<211> LENGTH: 954
<212> TYPE: DNA
<213> ORGANISM: Mus musculus

<400> SEQUENCE: 6
atgtcgagcc tcggcggtgg ctcccaggac gccggtggca gtagcagcag cagtaacacc     60
aatagcagca gtggcagtgg ccaaaaggca ggaggaacag acaaaagtac cgcggtggcc    120
gccaccacgg cgccgacctc cgtggcagac gatgccccac ccctgagcg tcggaacaag    180 agcggtatca tcagtgaacc cctcaacaag agcctgcggc gctcccgacc actctctcac    240
tactcttcct ttggtagcag tggtggcggc ggaagcatga tgggggtgga gtctgctgac    300
aaggcagcgg cagccgcagc ctccctattg ccaatggtc atgacctggc tgcggccatg    360
gcagtggaca aaagcaaccc tacctcaaag cacaaaagtg gtgctgtggc cagcctgctg    420
agcaaggcag agagggccac agagctggca gctgagggac agctgacgct gcagcagttt    480
gcacagtcca cagagatgct aaagcgcgtg gtgcaggaac acctgccact gatgagtgag    540
gccggtgccg gcctgcctga catggaggct gtggccggcg ccgaagccct caatggccag    600
tccgacttcc cctatctggg cgctttcccc atcaatccag gcctcttcat catgacccca    660
gctggcgtgt tcctggctga gagtgcactg acatggctg gctggccga gtaccccatg    720 cagggagagc tggcttccgc catcagctca ggcaagaaga agcggaaacg ctgcggcatg    780
tgtgcgccct gccggcggcg catcaactgt gagcagtgca gcagttgtag gaaccgaaag    840
actggccatc agatttgcaa attcagaaag tgtgaagaac tcaaaagaa gccttccgct    900 gctctggaga aggtgatgct tccgtcggga gccgccttcc ggtggtttca gtga          954

<210> SEQ ID NO 7
<211> LENGTH: 1447
<212> TYPE: RNA
<213> ORGANISM: Mus musculus

<400> SEQUENCE: 7
acugcuggcg gcuggagcgg agcgcaccgc ggcgguggug cccagagcgg agcgcagcuc     60
ccugccccgc cccuccccu cggccucgcg gcgacggcgg cgguggcggc uuggacgacu    120
cggagagccg agugaagaca uuccaccug acaccugac caugugccug cccugagcag    180
cgaggcccac caggcaucuc uguugugggc agcagggcca gguccuuguc uguggacccu    240
cggcaguugg caggcucccu cugcagugg gucuggccu cggccccacc augucgagcc    300
ucggcggugg cucccaggau gccggcggca guagcagcag cagcaccaau ggcagcggug    360
```

```
gcaguggcag caguggccca aaggcaggag cagcagacaa gagugcagug guggcugccg    420
ccgcaccagc cucaguggca gaugacacac cacccccga gcgucggaac aagagcggua    480
ucaucaguga gccccucaac aagagccugc gccgcucccg cccgcucucc cacuacucuu    540
cuuuuggcag caguggugu aguggcggug gcagcaugau gggcggagag ucugcugaca    600
aggccacugc ggcugcagcc gcugccuccc uguuggccaa ugggcaugac cuggcggcgg    660
ccauggcggu ggacaaaagc aacccuaccu caaagcacaa aaguggugcu guggccagcc    720
ugcugagcaa ggcagagcgg gccacggagc uggcagccga gggacagcug acgcugcagc    780
aguuugcgca guccacagag augcugaagc gcguggugca ggagcaucuc ccgcugauga    840
gcgaggcggg ugcuggccug ccugacaugg aggcuguggc aggugccgaa gcccucaaug    900
gccaguccga cuuccccuac cugggcgcuu uccccaucaa cccaggccuc uucauuauga    960 cccggcagg uguguuccug gccgagagcg cgcugcacau ggcgggccug gcugaguacc   1020
ccaugcaggg agagcuggcc ucugccauca gcuccggcaa gaagaagcgg aaacgcugcg   1080
gcaugugcgc gcccugccgg cggcgcauca acugcgagca gugcagcagu guaggaauc   1140 gaaagacugg ccaucagauu ugcaaauuca gaaaauguga ggaacucaaa aagaagccuu   1200
ccgcugcucu ggagaaggug augcuuccga cgggagccgc cuccggugg uuucagugac   1260 ggcggcggaa cccaaagcug cccucucccgu gcaaugucac ugcucgugug gucuccagca   1320
agggauucgg gcgaagacaa acggaugcac ccgucuuuag aaccaaaaau auucucuac   1380 agauuucauu ccuguuuuua uauauauauu uuuguugc guuuuaacau ucccacgucc   1440
cuagcau                                                             1447
```

<210> SEQ ID NO 8
<211> LENGTH: 28
<212> TYPE: DNA
<213> ORGANISM: Artificial
<220> FEATURE:
<223> OTHER INFORMATION: forward primer

<400> SEQUENCE: 8
ggaattccat atgtcgagcc tcggcggt                                        28

<210> SEQ ID NO 9
<211> LENGTH: 27
<212> TYPE: DNA
<213> ORGANISM: Artificial
<220> FEATURE:
<223> OTHER INFORMATION: reverse primer

<400> SEQUENCE: 9
cgcggatcct cactgaaacc accggaa                                         27

<210> SEQ ID NO 10
<211> LENGTH: 27
<212> TYPE: DNA
<213> ORGANISM: Artificial
<220> FEATURE:
<223> OTHER INFORMATION: forward primer

<400> SEQUENCE: 10
gctcagacta tgtcgagcct cggcggt                                         27

<210> SEQ ID NO 11
<211> LENGTH: 30
<212> TYPE: DNA
<213> ORGANISM: Artificial

```
<220> FEATURE:
<223> OTHER INFORMATION: reverse primer

<400> SEQUENCE: 11
cgcggatcct cactgaaacc accggaaggc                                          30

<210> SEQ ID NO 12
<211> LENGTH: 21
<212> TYPE: RNA
<213> ORGANISM: Artificial
<220> FEATURE:
<223> OTHER INFORMATION: Idbf siRNA

<400> SEQUENCE: 12
uuguaggaau cgaaagacuu u                                                   21

<210> SEQ ID NO 13
<211> LENGTH: 21
<212> TYPE: RNA
<213> ORGANISM: Artificial
<220> FEATURE:
<223> OTHER INFORMATION: Idbf siRNA

<400> SEQUENCE: 13
agucuuucga uuccuacaau u                                                   21

<210> SEQ ID NO 14
<211> LENGTH: 21
<212> TYPE: RNA
<213> ORGANISM: Artificial
<220> FEATURE:
<223> OTHER INFORMATION: Idbf siRNA

<400> SEQUENCE: 14
gcaguuugcg caguccacau u                                                   21

<210> SEQ ID NO 15
<211> LENGTH: 21
<212> TYPE: RNA
<213> ORGANISM: Artificial
<220> FEATURE:
<223> OTHER INFORMATION: Idbf siRNA

<400> SEQUENCE: 15
uguggacugc gcaaacugcu u                                                   21

<210> SEQ ID NO 16
<211> LENGTH: 22
<212> TYPE: DNA
<213> ORGANISM: Artificial
<220> FEATURE:
<223> OTHER INFORMATION: forward primer

<400> SEQUENCE: 16
cagagtaaag acatttccac gt                                                  22

<210> SEQ ID NO 17
<211> LENGTH: 20
<212> TYPE: DNA
<213> ORGANISM: Artificial
<220> FEATURE:
<223> OTHER INFORMATION: reverse primer

<400> SEQUENCE: 17
gctctgactt ttagggcagt                                                     20
```

```
<210> SEQ ID NO 18
<211> LENGTH: 28
<212> TYPE: DNA
<213> ORGANISM: Artificial
<220> FEATURE:
<223> OTHER INFORMATION: forward primer for upstream

<400> SEQUENCE: 18
gctctagact atgtcgagcc tcggcggt                                          28

<210> SEQ ID NO 19
<211> LENGTH: 25
<212> TYPE: DNA
<213> ORGANISM: Artificial
<220> FEATURE:
<223> OTHER INFORMATION: reverse primer for upstream

<400> SEQUENCE: 19
tgagttcctc attcctacaa ctgct                                             25

<210> SEQ ID NO 20
<211> LENGTH: 25
<212> TYPE: DNA
<213> ORGANISM: Artificial
<220> FEATURE:
<223> OTHER INFORMATION: forward primer for downstream

<400> SEQUENCE: 20
ttgtaggaat gaggaactca aaaag                                             25

<210> SEQ ID NO 21
<211> LENGTH: 30
<212> TYPE: DNA
<213> ORGANISM: Artificial
<220> FEATURE:
<223> OTHER INFORMATION: reverse primer for downstream

<400> SEQUENCE: 21
cgcggatcct cactgaaacc accggaaggc                                        30

<210> SEQ ID NO 22
<211> LENGTH: 21
<212> TYPE: RNA
<213> ORGANISM: Artificial
<220> FEATURE:
<223> OTHER INFORMATION: Fgf 18 siRNA

<400> SEQUENCE: 22
uguggacuuc cgcauccacu u                                                 21

<210> SEQ ID NO 23
<211> LENGTH: 21
<212> TYPE: RNA
<213> ORGANISM: Artificial
<220> FEATURE:
<223> OTHER INFORMATION: Fgf 18 siRNA

<400> SEQUENCE: 23
guggaugcgg aaguccacau u                                                 21

<210> SEQ ID NO 24
<211> LENGTH: 21
<212> TYPE: RNA
<213> ORGANISM: Artificial
<220> FEATURE:
<223> OTHER INFORMATION: Fgf 18 siRNA
```

```
<400> SEQUENCE: 24
gcagcugcgc uuguaccagu u                                              21

<210> SEQ ID NO 25
<211> LENGTH: 21
<212> TYPE: RNA
<213> ORGANISM: Artificial
<220> FEATURE:
<223> OTHER INFORMATION: Fgf 18 siRNA

<400> SEQUENCE: 25
cugguacaag cgcagcugcu u                                              21

<210> SEQ ID NO 26
<211> LENGTH: 26
<212> TYPE: PRT
<213> ORGANISM: Artificial
<220> FEATURE:
<223> OTHER INFORMATION: PolyR-DBMP

<400> SEQUENCE: 26

Arg Arg Arg Arg Arg Arg Arg Arg Gly Gly Gly Gly Arg Lys Thr Gly
1               5                   10                  15

His Gln Ile Cys Lys Phe Arg Lys Cys Lys
            20                  25

<210> SEQ ID NO 27
<211> LENGTH: 29
<212> TYPE: PRT
<213> ORGANISM: Artificial
<220> FEATURE:
<223> OTHER INFORMATION: HIV(Tat)-DBMP

<400> SEQUENCE: 27

Tyr Gly Arg Lys Lys Arg Arg Gln Arg Arg Gly Gly Gly Gly Arg
1               5                   10                  15

Lys Thr Gly His Gln Ile Cys Lys Phe Arg Lys Cys Lys
            20                  25

<210> SEQ ID NO 28
<211> LENGTH: 8
<212> TYPE: PRT
<213> ORGANISM: Artificial
<220> FEATURE:
<223> OTHER INFORMATION: PolyR8

<400> SEQUENCE: 28

Arg Arg Arg Arg Arg Arg Arg Arg
1               5

<210> SEQ ID NO 29
<211> LENGTH: 11
<212> TYPE: PRT
<213> ORGANISM: Artificial
<220> FEATURE:
<223> OTHER INFORMATION: HIV-Tat

<400> SEQUENCE: 29

Tyr Gly Arg Lys Lys Arg Arg Gln Arg Arg
1               5                   10
```

USE OF IDBF

CROSS-REFERENCE TO THE RELATED APPLICATIONS

This application is a national stage of international application No. PCT/KR2009/004338, filed on Aug. 3, 2009, and claims the benefit of priority under 35 USC 119 to Korean patent application No. 10-2008-0076128, filed on Aug. 4, 2008, the entire contents of which are incorporated herein by reference.

TECHNICAL FIELD

The present invention relates to an inhibitor of dishevelled (Dvl) and bone formation (Idbf) which is a novel Dvl-binding protein that binds to Dvl to inhibit signal transduction carried out through a Wnt/β-catenin signaling pathway, a gene for coding for the same, the use thereof, and the use as an inhibitor of Idbf.

BACKGROUND ART

A Wnt/β-catenin signaling pathway is a signaling pathway which plays a critical role in the development, growth and homeostasis of vertebrate animals. An abnormal Wnt/β-catenin signaling pathway causes various diseases including cancer and osteoporosis. Activation of the Wnt/β-catenin signaling pathway is initiated from binding a receptor, Frizzled (Fz), and a co-receptor, lipoprotein receptor-related protein 5 and 6 (LRP 5/6), to a ligand, Wnt. A component protein, Dvl, of the Wnt/β-catenin signaling pathway present in the cytoplasm functions to transmit a signal generated from the binding of Wnt to Fz and LRP5/6 to a β-catenin destruction complex serving as a protein complex, and the signal transduction by Dvl serves to facilitate dissociation of the β-catenin destruction complex, thereby blocking polyubiquitination of a core factor, β-catenin, of the Wnt/β-catenin signaling pathway and thus destroying the β-catenin. Therefore, as the β-catenin in the cytoplasm is increased in amount, some of the β-catenin moves into cell nuclei, thereby facilitating expression of target genes having β-catenin transcriptional activities.

Dvl has three evolutionarily conserved functional domains. Among these functional domains, a Post Synaptic Density-95, discs-large and Zonula occludens-1 (PDZ) domain consists of approximately 90 bases. Some Dvl-associated proteins binding to Dvl function in such a PDZ domain regulate the Wnt/β-catenin signaling pathway.

DISCLOSURE

Technical Problem

Therefore, an object of the present invention is to find a novel Dvl-associated protein and characterize functions of the Dvl-associated protein.

Technical Solution

One aspect of the present invention provides an inhibitor of Dvl and bone formation (Idbf) which is a novel Dvl-binding protein that binds to Dvl to inhibit signal transduction carried out through a Wnt/β-catenin signaling pathway.

Another aspect of the present invention also provides the use of Idbf for manufacturing a medicine that inhibits the signal transduction carried out through the Wnt/β-catenin signaling pathway, a pharmaceutical composition for inhibiting the signal transduction carried out through the Wnt/β-catenin signaling pathway, which includes the Idbf, and a method of inhibiting the signal transduction carried out through the Wnt/β-catenin signaling pathway, which includes administering an effective amount of the Idbf to a subject.

Still another aspect of the present invention also provides the use of an Idbf activator for manufacturing a medicine that inhibits signal transduction carried out through a Wnt/β-catenin signaling pathway, a pharmaceutical composition for inhibiting the signal transduction carried out through the Wnt/β-catenin signaling pathway, which includes the Idbf activator, and a method of inhibiting the signal transduction carried out through the Wnt/β-catenin signaling pathway, which includes administering an effective amount of the Idbf activator to a subject.

Yet another aspect of the present invention also provides the use of an Idbf inhibitor for manufacturing a medicine that activates signal transduction carried out through a Wnt/β-catenin signaling pathway, a pharmaceutical composition for activating the signal transduction carried out through the Wnt/β-catenin signaling pathway, which includes the Idbf inhibitor, and a method of activating the signal transduction carried out through the Wnt/β-catenin signaling pathway, which includes administering an effective amount of the Idbf inhibitor to a subject.

Yet another aspect of the present invention also provides the use of Idbf for screening a medicine that inhibits signal transduction carried out through a Wnt/β-catenin signaling pathway, a composition for screening a medicine that inhibits the signal transduction carried out through the Wnt/β-catenin signaling pathway, which includes the Idbf, and a method of screening a medicine that inhibits the signal transduction carried out through the Wnt/β-catenin signaling pathway, which includes contacting the Idbf with a candidate and determining whether the candidate inhibits or accelerates activities of the Idbf.

Yet another aspect of the present invention also provides the use of Idbf for screening a medicine that activates signal transduction carried out through a Wnt/β-catenin signaling pathway, a composition for screening a medicine that activates the signal transduction carried out through the Wnt/β-catenin signaling pathway, which includes the Idbf, and a method of screening a medicine that activates the signal transduction carried out through the Wnt/β-catenin signaling pathway, which includes contacting the Idbf to a candidate and determining whether the candidate inhibits or accelerates activities of the Idbf.

Advantageous Effects

According to the present invention, it was found that Idbf is expressed according to an activation signal in the Wnt/β-catenin signaling pathway and binds to Dvl to block signal transduction carried out through the Wnt/β-catenin signaling pathway. Therefore, the Idbf can be used to prepare medicines that inhibit the signal transduction carried out through the Wnt/β-catenin signaling pathway. On the other hand, an Idbf inhibitor may be used prepare medicines that activate the signal transduction carried out through the Wnt/β-catenin signaling pathway.

DESCRIPTION OF DRAWINGS

The file of this patent contains at least one drawing executed in color. Copies of this patent with color drawings will be provided by the Office upon request and payment of the necessary fee.

These and other features, aspects, and advantages of preferred embodiments of the present invention will be more fully described in the following detailed description, taken accompanying drawings. In the drawings:

FIG. 8 is a diagram showing changes in weights (8A), bone densities (8B), femoral bone densities (8C) and femoral lengths (8D) of mice according to the knockout of the Idbf.

BEST MODE

Hereinafter, exemplary embodiments of the present invention will be described in further detail.

The present invention provides an inhibitor of dishevelled (Dvl) and bone formation (Idbf) which is a novel Dvl binding protein that bind to Dvl to inhibit signal transduction carried out through a Wnt/β-catenin signaling pathway.

The Wnt/β-catenin signaling pathway is one of important cell signaling pathways that participate in development, bone formation, transformation of cells, etc. There is little research on inhibitors in the Wnt/β-catenin signaling pathway, compared to activators. The present inventors have conducted attempts to find a novel inhibitor of the Wnt/β-catenin signaling pathway and characterize functions of the novel inhibitor. Therefore, in the procedure of screening proteins similar to Idax, which is a Dvl-associated protein known as the inhibitor in the Wnt/β-catenin signaling pathway, the present inventors have found Idbf which is a novel Dvl-associated protein that binds to Dvl to inhibit the signal transduction carried out in the Wnt/β-catenin signaling pathway. Idbf was found to have an amino acid sequence set forth in SEQ ID NO: 1. Here, the Idbf shares an evolutionarily highly conserved carboxyl terminal domain with Idax, which provides a basis that can be used to expect functional similarity between two proteins. An aminoacyl terminal domain of the Idbf consisting of approximately 130 amino acids has a unique structure. Here, the aminoacyl terminal domain is considered to contribute to interaction with a certain protein so as to perform functions of the Idbf. Also, the Idbf has an amino acid sequence (RKTGHQICKFRKC) (Dvl minimal binding peptide, DBMP, SEQ ID NO: 4) consisting of 13 amino acids, which has been known to be an important motif (a functional domain) in which Idax interacts with Dvl.

Figure 1:
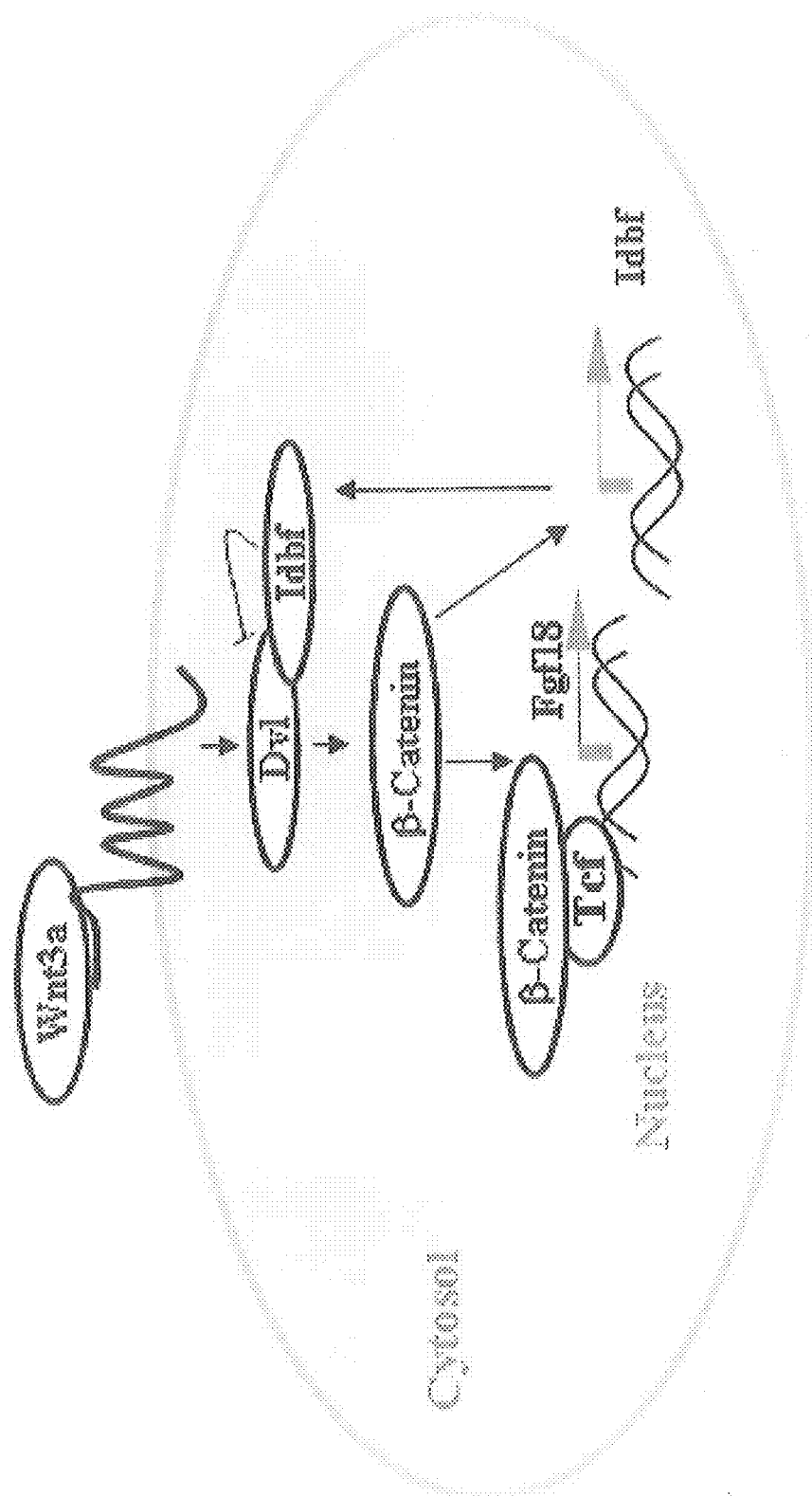
FIG. 1 is a schematic view showing a model for action mechanism of Idbf identified in the present invention.

FIG. 1 shows a model for action mechanism of Idbf identified in the present invention. As seen from FIG. 1, activation of a signaling pathway by Wnt3a induces expression of Fgf18 and Idbf. At the same time, the Wnt3a enhances interaction of the Idbf with Dvl-1. That is, the Idbf is activated by the Wnt3a. In turn, activation of the Idbf leads to inhibition of the Wnt/β-catenin signaling pathway. For the functions of the Idbf, importance of the Idbf-Dvl-1 interaction was confirmed from the fact that a mutant protein, IdbfΔDBMP, in which a motif interacting with Dvl-1 is deleted, loses its innate functions. An increase in Idbf protein and mRNA by treatment of Wnt3a indicates that Idbf is increasingly transcribed by the activation of the Wnt/β-catenin signaling pathway, and then functions as a negative feedback regulator that, in turn, inhibits the Wnt/β-catenin signaling pathway.

The Idbf binds to Dvl to inhibit signal transduction carried out through the Wnt/β-catenin signaling pathway. An abnormal Wnt/β-catenin signaling pathway causes various diseases including cancer and osteoporosis. Therefore, when expression of the Idbf that blocks the signal transduction by a component protein, Dvl, of the Wnt/β-catenin signaling pathway is regulated, it is possible to treat diseases caused by the abnormal Wnt/β-catenin signaling pathway.

Therefore, the present invention provides the use of Idbf for manufacturing a medicine that inhibits signal transduction carried out through a Wnt/β-catenin signaling pathway, a pharmaceutical composition for inhibiting the signal transduction carried out through the Wnt/β-catenin signaling pathway, which includes the Idbf, and a method of inhibiting the signal transduction carried out through the Wnt/β-catenin signaling pathway, which includes administering an effective amount of the Idbf to a subject.

In the present invention, 'Idbf' used to inhibit the signal transduction carried out through the Wnt/β-catenin signaling pathway may be in various shapes such as an Idbf protein, an Idbf gene or a vector including an Idbf gene, mRNA of the Idbf, etc., and may be suitably interpreted according to situations. For example, the shapes of the Idbf may be an Idbf protein, an Idbf gene or a vector including an Idbf gene, depending on the route of administration into subjects. When the Idbf protein is administered, the signal transduction through Dvl may be directly blocked, and when the Idbf gene or the vector including the Idbf gene is administered, an expression level of the Idbf in cells is increased to block the signal transduction through Dvl.

According to one embodiment of the present invention, the Idbf protein may have an amino acid sequence set forth in SEQ ID NO: 1 or 5, the Idbf gene may have a nucleic acid sequence set forth in SEQ ID NO: 2 or 6, and mRNA of the Idbf may have a nucleic acid sequence set forth in SEQ ID NO: 3 or 7, but the present invention is not limited thereto.

In the present invention, it is understood that variants or fragments of the Idbf protein, Idbf gene and the mRNA of the Idbf, all of which have substantially the same activities as the Idbf protein, Idbf gene, and the mRNA of the Idbf, are included in the Idbf protein, Idbf gene and the mRNA of the Idbf.

In order to inhibit the signal transduction carried out through the Wnt/β-catenin signaling pathway, an 'Idbf activator' may be used instead of the 'Idbf.' Therefore, the present invention also provides the use of an Idbf activator for manufacturing a medicine that inhibits signal transduction carried out through a Wnt/β-catenin signaling pathway, a pharmaceutical composition for inhibiting the signal transduction carried out through the Wnt/β-catenin signaling pathway, which includes the Idbf activator, and a method of inhibiting the signal transduction carried out through the Wnt/β-catenin signaling pathway, which includes administering an effective amount of the Idbf activator to a subject. In the present invention, the term 'Idbf activator' includes all materials that activate binding of an Idbf protein to Dvl. That is, the Idbf activator includes all materials that increase expression of Idbf so as to increase an amount of the Idbf protein binding to Dvl, or accelerate binding of the Idbf protein to Dvl.

The inhibition of the signal transduction carried out through the Wnt/β-catenin signaling pathway by the Idbf or the Idbf activator is performed by binding of the Idbf to Dvl to block the signal transduction through Dvl. In this case, excessive activation of the Wnt/β-catenin signaling pathway may cause diseases such as familial adenomatous polyposis (Kinzler, et al., (1991), Identification of FAP locus genes from chromosome 5q21. Science 253, 661-665), colon cancer (Kinzler and Vogelstein, (1996), Lessons from hereditary colorectal cancer. Cell 87, 159-170), liver cancer, melanoma, endometrial cancer, prostate cancer (Morin, (1999), beta-catenin signaling and cancer. Bioessays 21, 1021-1030; Polakis, (1999), The oncogenic activation of beta-catenin. Curr Opin Genet Dev 9, 15-21), desmoid tumor, pancreatic cancer, stomach cancer, ovarian cancer (Polakis, (2000), Wnt signaling and cancer. Genes Dev 14, 1837-1851), Dupuytren's skin disease (Varallo, et al., (2003), Beta-catenin expression in Dupuytren's disease: potential role for cell-matrix interactions in modulating beta-catenin levels in vivo and in vitro. Oncogene 22, 3680-3684), osteoarthritis (Loughlin, et al., (2004), Functional variants within the secreted frizzled-related protein 3 gene are associated with hip osteoarthritis in females. Proc Natl Acad Sci USA 101, 9757-9762), autosomal dominant osteopetrosis, van Buchem's disease, hyperostosis, osteosclerosis (Johnson, et al., (2004), LRP5 and Witt signaling: a union made for bone. J Bone Miner Res 19, 1749-1757; van Wesenbeeck, et al., (2003), Six novel missense mutations in the LDL receptor-related protein 5 (LRP5) gene in different conditions with an increased bone density. Am J Hum Genet 72, 763-771), arteriosclerosis (Shioi, et al., (1995), Beta-glycerophosphate accelerates calcification in cultured bovine vascular smooth muscle cells. Arterioscler Thromb Vase Biol 15, 2003-2009), cardiac hypertrophy (van Gijn, et al., (2002), The wnt-frizzled cascade in cardiovascular disease. Cardiovasc Res 55, 16-24), and schizophrenia (Miyaoka, et al., (1999), Increased expression of Wnt-1 in schizophrenic brains, Schizophr Res 38, 1-6) and the like. Therefore, when the signal transduction of the Wnt/β-catenin signaling pathway through Dvl is inhibited by the Idbf or Idbf activator, these diseases may be effectively prevented or treated. Accordingly, one embodiment of the present invention provides the use of Idbf or an Idbf activator for manufacturing a medicine to prevent or treat a disease such as familial adenomatous polyposis, colon cancer, liver cancer, melanoma, endometrial cancer, prostate cancer, desmoid tumor, pancreatic cancer, stomach cancer, ovarian cancer, Dupuytren's skin disease, osteoarthritis, autosomal dominant osteopetrosis, van Buchem's disease, hyperostosis, osteosclerosis, arteriosclerosis, cardiac hypertrophy, or schizophrenia, a pharmaceutical composition for preventing or treating a disease such as familial adenomatous polyposis, colon cancer, liver cancer, melanoma, endometrial cancer, prostate cancer, desmoid tumor, pancreatic cancer, stomach cancer, ovarian cancer, Dupuytren's skin disease, osteoarthritis, autosomal dominant osteopetrosis, van Buchem's disease, hyperostosis, osteosclerosis, arteriosclerosis, cardiac hypertrophy, or schizophrenia, which includes an effective amount of the Idbf or Idbf activator, and a method of preventing or treating a disease such as familial adenomatous polyposis, colon cancer, liver cancer, melanoma, endometrial cancer, prostate cancer, desmoid tumor, pancreatic cancer, stomach cancer, ovarian cancer, Dupuytren's skin disease, osteoarthritis, autosomal dominant osteopetrosis, van Buchem's disease, hyperostosis, osteosclerosis, arteriosclerosis, cardiac hypertrophy, and schizophrenia, which includes administering an effective amount of the Idbf or Idbf activator to a subject.

Also, the present invention provides the use of an Idbf inhibitor for manufacturing a medicine that activates signal transduction carried out through a Wnt/β-catenin signaling pathway, a pharmaceutical composition for activating the signal transduction carried out through the Wnt/β-catenin signaling pathway, which includes the Idbf inhibitor, and a method of activating the signal transduction carried out through the Wnt/β-catenin signaling pathway, which includes administering an effective amount of the Idbf inhibitor to a subject.

The activation of the signal transduction carried out through the Wnt/β-catenin signaling pathway of the Idbf is performed by inhibiting binding of the Idbf to Dvl to cause the signal transduction through Dvl. In this case, excessive inhibition of the Wnt/β-catenin signaling pathway may cause diseases such as osteoporosis (Gong, et al., (2001), LDL receptor-related protein 5 (LRP5) affects bone accrual and eye development. Cell 107, 513-523), Alzheimer's disease (Caricasole, et al., (2003), The Wnt pathway, cell-cycle activation and beta-amyloid: novel therapeutic strategies in Alzheimer's disease; Trends Pharmacal Sci 24, 233-238), myocardial infarction (van Gijn, Damen, Smits and Blankesteijn, (2002), The wnt-frizzled cascade in cardiovascular disease. Cardiovasc Res 55, 16-24), and familial exudative vitreoretinopathy (Kondo, et al., (2003), Frizzled 4 gene (FZD4) mutations in patients with familial exudative vitreoretinopathy with variable expressivity. Br J Ophthalmol 87, 1291-1295). Therefore, when the signal transduction of the Wnt/β-catenin signaling pathway through Dvl is activated by the Idbf inhibitor, these diseases may be effectively prevented or treated. Accordingly, one embodiment of the present invention provides the use of an Idbf inhibitor for manufacturing a medicine for prevention or treatment of a disease such as osteoporosis, Alzheimer's disease, myocardial infarction, or familial exudative vitreoretinopathy, a pharmaceutical composition for preventing or treating a disease such as osteoporosis, Alzheimer's disease, myocardial infarction, or familial exudative vitreoretinopathy, which includes the Idbf inhibitor, and a method of preventing or treating a disease such as osteoporosis, Alzheimer's disease, myocardial infarction, or familial exudative vitreoretinopathy, which includes administering an effective amount of the Idbf inhibitor to a subject. Also as seen from the following examples, when the signal transduction of the Wnt/β-catenin signaling pathway through Dvl is activated, a bone or cartilage is increased in length and a bone is increased in thickness, thereby inducing growth of a bone or cartilage, accelerating recovery of bone fracture, or inducing an increase in bone density. Therefore, one embodiment of the present invention provides the use of an Idbf inhibitor for inducing growth of a bone or cartilage, accelerating recovery of bone fracture or inducing an increase in bone density, a pharmaceutical composition for inducing growth of a bone or cartilage, accelerating recovery of bone fracture or inducing an increase in bone density, which includes the Idbf inhibitor, and a method of inducing growth of a bone or cartilage, accelerating recovery of bone fracture or inducing an increase in bone density, which includes administering an effective amount of the Idbf inhibitor to a subject.

In addition to the diseases associated with the Wnt/β-catenin signaling pathway illustrated in this specification of the present invention, diseases caused by the excessive inhibition or activation of the signal transduction through the Wnt/β-catenin signaling pathway have been known in the art. As the fact that the Idbf binds to Dvl to regulate the Wnt/β-catenin signaling pathway is revealed in the present invention, a person of skill in the art may inhibit or activate the Idbf to prevent or treat diseases associated with the signal transduction of the Wnt/β-catenin signaling pathway.

For the prevention or treatment of the disease associated with the signal transduction through the Wnt/β-catenin signaling pathway, for example, effects of inhibition of Idbf expression or overexpression of the Idbf on the Wnt/β-catenin signaling pathway was examined for bone formation and differentiation of osteoblast in which the Wnt/β-catenin signaling pathway has been reported to play an important role in examples of the present invention. The method of inhibiting binding of the Idbf to Dvl includes a method of inhibiting expression of the Idbf instead of the use of the Idbf inhibitor, and the activation of the Idbf includes a method of overexpressing the Idbf. The experimental results showed that Idbf knockout mice have an increased bone density and longer bones due to the activation of the signal transduction carried out through the Wnt/β-catenin signaling pathway, compared to normal mice. The histological analysis of bones of the Idbf knockout mice showed that a bone plate in the bones is excessively activated. Meanwhile, the Idbf is increased in amount as the osteoblast is differentiated, and the overexpression of the Idbf served to inhibit the Wnt/β-catenin signaling pathway, and simultaneously hamper the differentiation of the osteoblast. This indicates that the Idbf functions as a feedback regulator for the Wnt/β-catenin signaling pathway and the osteoblast differentiation. Also, Fgf18, which has been known to be an important factor for cartilage formation and bone formation in stages of bone development and growth, was found to be a mediator important in regulating the osteoblast differentiation of Idbf. The overexpression of Idbf causes reduction in expression of Fgf18 as well as ALP. This indicates that the Idbf regulates the differentiation of the osteoblast through Fgf18. An arbitrary reduction through siRNA of the Fgf18 prevents an increase of ALP by Wnt3a, which indicates that the Fgf18 functions as a mediator for the osteoblast differentiation through the Wnt/β-catenin signaling pathway. In particular, expression levels of cyclin D and c-myc in the osteoblast are not changed regardless of treatment with Wnt3a, which indicates that the Fgf18 is highly specifically regulated by the Wnt3a in these cells.

In the present invention, the 'Idbf inhibitor' used to activate the signal transduction carried out through the Wnt/β-catenin signaling pathway includes all inhibitors that block binding of an Idbf protein to Dvl. According to the following examples, among amino acid sequences of the Idbf, an amino acid sequence (RKTGHQICKFRKC) set forth in SEQ ID NO: 4 was found to be a binding site to Dvl. Therefore, the Idbf inhibitor may be preferably designed to target a Dvl binding site having the amino acid sequence (RKTGHQICKFRKC) set forth in SEQ ID NO: 4 and a gene coding region coding for the Dvl binding site in the Idbf protein.

According to one embodiment of the present invention, the Idbf inhibitor may be an inhibitor that binds to an Idbf protein or a Dvl protein to block binding of the Idbf to Dvl. For example, the Idbf inhibitor may be a polypeptide having an amino acid sequence (RKTGHQICKFRKC) set forth in SEQ ID NO: 4. The polypeptide having the amino acid sequence (RKTGHQICKFRKC) set forth in SEQ ID NO: 4 is an antagonist that can bind to Dvl in competition with the Idbf, and may block binding of the Idbf to Dvl. According to the prior-art research (London, et al., (2004), Interaction between the internal motif KTXXXI of Idax and mDvl PDZ domain. Biochem Biophys Res Commun 322, 326-332), it was found that the 2.sup.nd (K), 3.sup.rd (T) and 7.sup.th (I) amino acids of SEQ ID NO: 4 are essential to bind to the Dvl protein. Therefore, a peptide having an improved binding affinity to the Dvl protein may be constructed through substitution of the amino acids other than the three amino acids. Therefore, variants of the polypeptide having the amino acid sequence (RKTGHQICKFRKC) set forth in SEQ ID NO: 4 are also considered to be included in the Idbf inhibitor of the present invention. In the present invention, the polypeptide having the amino acid sequence (RKTGHQICKFRKC) set forth in SEQ ID NO: 4 includes polypeptides that are chemically modified to facilitate penetration of the polypeptides into cells. This chemical modification may, for example, include insertion of a protein transduction domain (PTD). A PTD-introduced polypeptide may be prepared by adding a certain amino acid sequence of 10 to 20 amino acids (Matsushita and Matsui, (2005), Protein transduction technology. J Mol Med 83, 324-328). PTD is mainly composed of basic amino acids such as arginine or lysine, and representative examples of the PTD include poly R.sub.8 (RRRRRRRR) (SEQ ID NO: 28) or HIV-Tat (YGRKKRRQRRR) (SEQ ID NO: 29). The penetration into the cells may be induced by adding such a series of the amino acid sequence into the N-terminus or C-terminus of the amino acid sequence (RKTGHQICKFRKC) set forth in SEQ ID NO: 4. According to one embodiment of the present invention, the PTD-inserted polypeptide having the amino acid sequence set forth in SEQ ID NO: 4 may be a polypeptide having an amino acid sequence set forth in SEQ ID NO: 26 or SEQ ID NO: 27. Also, the Idbf inhibitor may be a compound that binds to an Idbf protein or a Dvl protein to block binding between the Idbf and the Dvl. Such a compound may be selected through the following screening method, and otherwise may be designed to have a structure similar to the polypeptide having the amino acid sequence (RKTGHQICKFRKC) set forth in SEQ ID NO: 4. Also, the Idbf inhibitor may be a polyclonal or monoclonal antibody against the Idbf or Dvl protein. Such a polyclonal antibody or monoclonal antibody may be produced using an antibody producing method known in the art.

According to another embodiment of the present invention, the Idbf inhibitor may be an inhibitor that blocks expression of the Idbf protein, or blocks binding of Idbf to Dvl by removing a base sequence of the Idbf coding for a Dvl binding site having the amino acid sequence (RKTGHQICKFRKC) set forth in SEQ ID NO: 4. For example, the Idbf inhibitor may be an antisense oligonucleotide, siRNA, shRNA or miRNA of the Idbf, or a vector containing the antisense oligonucleotide, the siRNA, the shRNA or the miRNA.

In the present invention, the term 'vector' means a genetic construct including exogenous DNA that is inserted into a genome to code for a polypeptide. The vector according to one embodiment of the present invention may be a vector in which a nucleic acid sequence coding for an Idbf gene is inserted into a genome, and examples of the vector include, for example, a DNA vector, a plasmid vector, a cosmid vector, a bacteriophage vector, a yeast vector, and a viral vector.

The pharmaceutical composition of the present invention may also further include an effective component that is known to inhibit or activate the signal transduction carried out through the Wnt/β-catenin signaling pathway.

In addition to the effective component, the pharmaceutical composition of the present invention may be prepared using a pharmaceutically suitable and physiologically available adjuvant. Here, a solubilizing agent such as an excipient, a disintegrating agent, a sweetening agent, a binding agent, a coating agent, a leavening agent, a lubricant, a glidant or a flavoring agent may be used as the adjuvant.

In addition to the effective component, the pharmaceutical composition according to one embodiment of the present invention may further include at least one pharmaceutically available carrier for administration, and may then be preferably formulated into a pharmaceutical composition.

For compositions to be formulated into a liquid solution, a pharmaceutically available carrier is sterile and suitable for in vivo use. The carrier used herein may include saline, sterile water, a Ringer's solution, buffered saline, an albumin injection, a dextrose solution, a maltodextrin solution, glycerol, ethanol and a mixture thereof, and a conventional additive such as an antioxidant, a buffer or a bacteriostatic agent may be added, when necessary. Also, a diluent, a dispersing agent, a surfactant, a binding agent and a lubricant may be further added, and then formulated into an injectable formulation such as an aqueous solution, a suspension or an emulsion, a pill, a capsule, a granule or a tablet. Furthermore, compositions may be preferably formulated according to the respective diseases or the components using a method disclosed in the literature (Remington's Pharmaceutical Science, Mack Publishing Company, Easton Pa.) as the suitable method known in the related art.

A pharmaceutical formulation type of the pharmaceutical composition according to the present invention may include a granule, an acidifier, a coated tablet, a tablet, a capsule, a suppository, syrup, a sap, a suspending agent, an emulsifying agent, drops or an injectable solution, and a sustained release formulation of active compounds.

The pharmaceutical composition of the present invention may be administered through a conventional route such as intravenous, intraarterial, intraabdominal, intramuscular, intrasternal, percutaneous, intranasal, inhalation, topical, rectal, oral, intraocular or blood route.

For the pharmaceutical composition of the present invention, an effective amount of an effective component means an amount of a component required to prevent or treat a disease or induce bone growth. Therefore, the effective amount of the effective component may be adjusted according to the kind of diseases, the severity of a disease, the kind and content of an effective component and other component in a composition, the kind of formulations, the age, body weight, general health status, sex and diet of a patient, the administration time, the route of administration, and the secretion rate of a composition, the treatment period, and various factors including medicines used together. For example, when the Idbf is administered to adult patients once or several times per day, an Idbf protein and an Idbf gene may be administered at doses of 0.1 ng/kg to 10 g/kg and 0.01 ng/kg to 10 g/kg, respectively. Also, when an Idbf activator is administered once or several times per day, the Idbf activator may be administered at a dose of 0.1 ng/kg to 10 g/kg, and when an Idbf inhibitor is administered once or several times per day, an antisense oligonucleotide, siRNA, shRNAi or miRNA of the Idbf inhibitor may be administered at a dose of 0.01 ng/kg to 10 g/kg. In addition, a compound may be administered at a dose of 0.1 ng/kg to 10 g/kg, and an antibody against the Idbf may be administered at a dose of 0.1 ng/kg to 10 g/kg.

In the present invention, the term 'subject' includes a human, an orangutan, a chimpanzee, a mouse, a rat, a dog, a cow, a chicken, a pig, a goat, a sheep, etc., but the present invention is not limited thereto.

Also, the present invention provides the use of Idbf for screening a medicine that inhibits signal transduction carried out through a Wnt/β-catenin signaling pathway, a composition for screening a medicine that inhibits the signal transduction carried out through the Wnt/β-catenin signaling pathway, which includes the Idbf, and a method of screening a medicine that inhibits the signal transduction carried out through the Wnt/β-catenin signaling pathway, which includes contacting the Idbf with a candidate and determining whether the candidate inhibits or accelerates activities of the Idbf.

As described above, the Idbf binds to Dvl to inhibit the signal transduction carried out through the Wnt/β-catenin signaling pathway. Therefore, a material that accelerates the expression of Idbf and the activities of the Idbf may be used as the medicine that inhibits the signal transduction carried out through the Wnt/β-catenin signaling pathway.

Also, the present invention provides the use of Idbf for screening a medicine that activates signal transduction carried out through a Wnt/β-catenin signaling pathway, a composition for screening a medicine that activates the signal transduction carried out through the Wnt/β-catenin signaling pathway, which includes the Idbf, and a method of screening a medicine that activates the signal transduction carried out through the Wnt/β-catenin signaling pathway, which includes contacting the Idbf with a candidate and determining whether the candidate inhibits or facilitates activities of the Idbf.

Also, as described above, the Idbf binds to Dvl to inhibit the signal transduction carried out through the Wnt/β-catenin signaling pathway. Therefore, a material that inhibits the expression of Idbf and the activities of the Idbf may be used as the medicine that activates the signal transduction carried out through the Wnt/β-catenin signaling pathway.

The 'Idbf' used to screen a medicine that inhibits or activates the signal transduction carried out through the Wnt/β-catenin signaling pathway may include an Idbf protein, an Idbf gene, mRNA of the Idbf, etc. In this case, it is understood that variants or fragments of the Idbf protein, Idbf gene and the mRNA of the Idbf, all of which have substantially the same activities as the Idbf protein, Idbf gene, and the mRNA of the Idbf, are included in the Idbf protein, Idbf gene and the mRNA of the Idbf.

Reaction between the Idbf and the candidate may be determined using conventional methods which are used to determine a protein-protein, protein-compound, DNA-DNA, DNA-RNA, DNA-protein, DNA-compound, RNA-protein, or RNA-compound reaction. For example, the reaction may be determined using a hybridization test for determining in vitro binding of an Idbf gene to a candidate, a method of measuring expression of the Idbf gene by means of a northern blotting assay, quantitative PCR and quantitative real-time PCR after reaction of a mammary cell with a material to be tested, a method of binding a reporter gene to the gene, introducing the gene into cells, reacting the gene with a material to be tested and measuring an expression rate of the reporter protein, a method of measuring activities of Idbf after reaction of an Idbf protein with a candidate, a yeast two-hybrid assay, screening of a phage-displayed peptide clone that binds to an Idbf protein, high throughput screening (HTS) using natural and chemical libraries, drug hit HTS, cell-based screening, or a screening method using a DNA array, etc.

In addition to the Idbf, the screening composition may include distilled water or a buffer which stably maintains a structure of a nucleic acid or a protein. For in vivo experiments, the screening composition may also include a cell expressing the Idbf, a cell containing a plasmid in which the Idbf is expressed from a promoter that can adjust a transcriptional rate, etc. In addition to the Idbf, the screening composition may also further include Dvl to determine reaction between the Idbf and a candidate.

In the screening method of the present invention, a material to be tested may include respective nucleic acids and proteins, other extracts or natural substances, compounds, etc. which may be assumed to be medicines that inhibit or activate the signal transduction carried out through the Wnt/β-catenin signaling pathway, or are randomly selected according to a conventional selection method.

As described above, when the Idbf is overexpressed, the signal transduction through the Wnt/β-catenin signaling pathway is excessively inhibited. Then, the excessive inhibition of the signal transduction may highly cause diseases such as osteoporosis, Alzheimer's disease, myocardial infarction, and familial exudative vitreoretinopathy. On the other hand, when the Idbf is underexpressed or a binding affinity to Dvl is low due to mutation of the Idbf, the signal transduction through the Wnt/β-catenin signaling pathway is excessively activated. Then, the overexpression of the signal transduction may highly cause diseases such as familial adenomatous polyposis, colon cancer, liver cancer, melanoma, endometrial cancer, prostate cancer, desmoid tumor, pancreatic cancer, stomach cancer, ovarian cancer, Dupuytren's skin disease, osteoarthritis, autosomal dominant osteopetrosis, van Buchem's disease, hyperostosis, osteosclerosis, arteriosclerosis, cardiac hypertrophy, and schizophrenia. Therefore, when an expression level of the Idbf or mutation of the Idbf is examined, the possibility of developing the diseases may be anticipated or diagnosed by assaying activation or inhibition of the signal transduction carried out through the Wnt/β-catenin signaling pathway.

Therefore, the present invention also provides a method of assaying activation or inhibition of the signal transduction carried out through the Wnt/β-catenin signaling pathway, which includes obtaining a protein sample expressed from tissues or cells of an animal, identifying the presence of Idbf in the obtained protein sample and quantifying the Idbf.

Also, the present invention provides a composition for assaying activation or inhibition of the signal transduction carried out through the Wnt/β-catenin signaling pathway, which includes an antibody against an Idbf protein.

Also, the present invention provides a method of assaying activation or inhibition of the signal transduction carried out through the Wnt/β-catenin signaling pathway, which includes obtaining a protein sample expressed from tissues or cells of an animal, reacting the obtained protein sample with an antibody against Idbf to determine expression of the Idbf and quantifying the Idbf.

The assaying methods may be used to quantitatively analyze the Idbf by color reaction of an analytic composition including an antibody against the Idbf with an extracted in vivo substance (a protein extract or plasma from cells or tissues, etc.) using an enzyme-linked immunosorbent assay (ELISA), or to assay the activation or inhibition of the signal transduction carried out through the Wnt/β-catenin signaling pathway using Idbf-specific histoimmunostaining of extracted in vivo tissues or cells. Also, the activation or inhibition of the signal transduction carried out through the Wnt/β-catenin signaling pathway may be assayed by comparing expression levels of the Idbf in extracted in vivo tissues or cells and a normal group and analyzing the expression levels in a protein level using a western blotting assay.

Also, the activation or inhibition of the signal transduction carried out through the Wnt/β-catenin signaling pathway may be, for example, assayed by (1) attaching a monoclonal antibody or a polyclonal antibody against Idbf to a gel-type support to prepare an immunoaffinity column, (2) quantifying the Idbf in a substance (a protein extract or plasma from cells or tissues, etc.), which is extracted in vivo using the immunoaffinity column of step (1), using an HPLC method, and (3) comparing and analyzing the quantitative results.

The antibody against the Idbf may be produced according to a conventional method of producing a monoclonal or polyclonal antibody known in the art.

In general, the antibody against the Idbf may be quantitatively analyzed by color reaction of a substrate with a secondary antibody with which an enzyme such as alkaline phosphatase (AP) or horseradish peroxidase (HRP) is conjugated, or may be quantitatively analyzed using a secondary antibody in which an enzyme such as AP or HRP is directly conjugated with the Idbf.

Also, the present invention provides a composition for assaying activation or inhibition of signal transduction carried out through a Wnt/β-catenin signaling pathway, which includes a PCR primer or a probe for an Idbf gene.

The activation or inhibition of the signal transduction carried out through the Wnt/β-catenin signaling pathway may be assayed by performing RT-PCR or quantitative RT-PCR using primers for the Idbf gene to compare an expression level of the Idbf with that of a normal group. Also, the activation or inhibition of the signal transduction carried out through the Wnt/β-catenin signaling pathway may be assayed by performing a northern blotting assay using a probe for the Idbf gene to compare an expression level of the Idbf with that of a normal group.

The activation or inhibition of the signal transduction carried out through the Wnt/β-catenin signaling pathway may be assayed by allowing a composition for assaying activation or inhibition of the signal transduction carried out through the Wnt/β-catenin signaling pathway to react an extracted in vivo substance (RNA extracted from cells or tissues) (RT-PCR or quantitative RT-PCR or northern blotting) to compare to a normal group.

Also, the present invention provides a method of assaying activation or inhibition of signal transduction carried out though a Wnt/β-catenin signaling pathway, which includes obtaining an RNA sample expressed from tissues or cells of an animal, reacting the obtained RNA sample with a primer or probe for Idbf to determine expression of the Idbf and quantifying the Idbf.

Also, the present invention provides a method of assaying activation or inhibition of signal transduction carried out though a Wnt/β-catenin signaling pathway, which includes obtaining a protein sample expressed from tissues or cells of an animal, and determining mutation of Idbf from the obtained protein sample.

The determination of the mutation of the Idbf from the obtained protein sample may be, for example, performed by separating the Idbf from the protein sample, reacting the separated Idbf with an antibody against a Dvl binding site having an amino acid sequence (RKTGHQICKFRKC) set forth in SEQ ID NO: 4, and examining binding of the Idbf to the antibody to determine whether or not the Dvl binding site to the Idbf is mutated.

Also, the present invention provides an Idbf knockdown mouse in which the signal transduction of the Wnt/β-catenin signaling pathway is activated. Such an Idbf knockout mouse may be prepared by deactivating an Idbf gene according to a known method of preparing a knockdown mouse. In the following examples, the Idbf knockout mouse in which the signal transduction of the Wnt/β-catenin signaling pathway is activated was prepared by deactivating exon 2 of an Idbf gene on chromosome 18 using a homologues recombination technique, but the present invention is not limited thereto.

In the present invention, the details associated with the genetic engineering technology may be more apparent from the contents disclosed in the literature by Sambrook (Sambrook, et al, Molecular Cloning, A Laboratory Manual, Cold Spring Harbor laboratory Press, Cold Spring Harbor, N.Y. (2001)) and the literature by Frederick (Frederick M. Ausubel et al., Current protocols in molecular biology volume 1, 2, 3, John Wiley & Sons, Inc. (1994)).

Mode for Invention

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

1, Identification of Idbf

Figure 2:
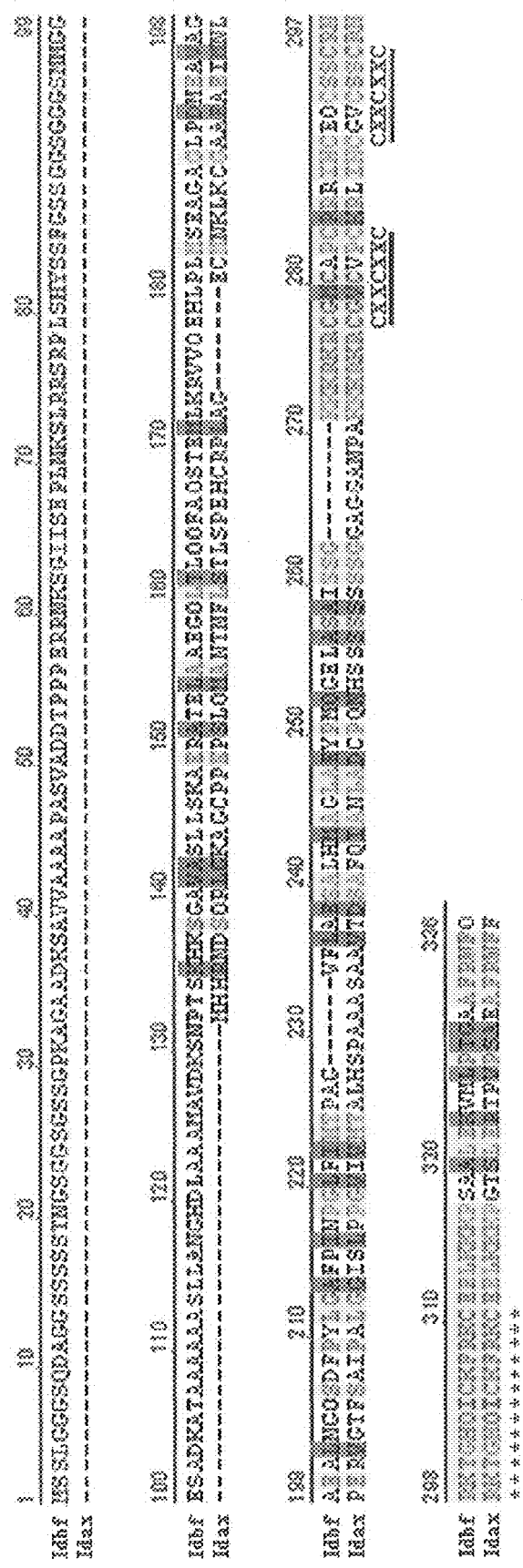
FIG. 2 shows the results obtained by comparing amino acid sequences of human Idbf and Idax using AlingX software (Invitrogen).
Figure 3:
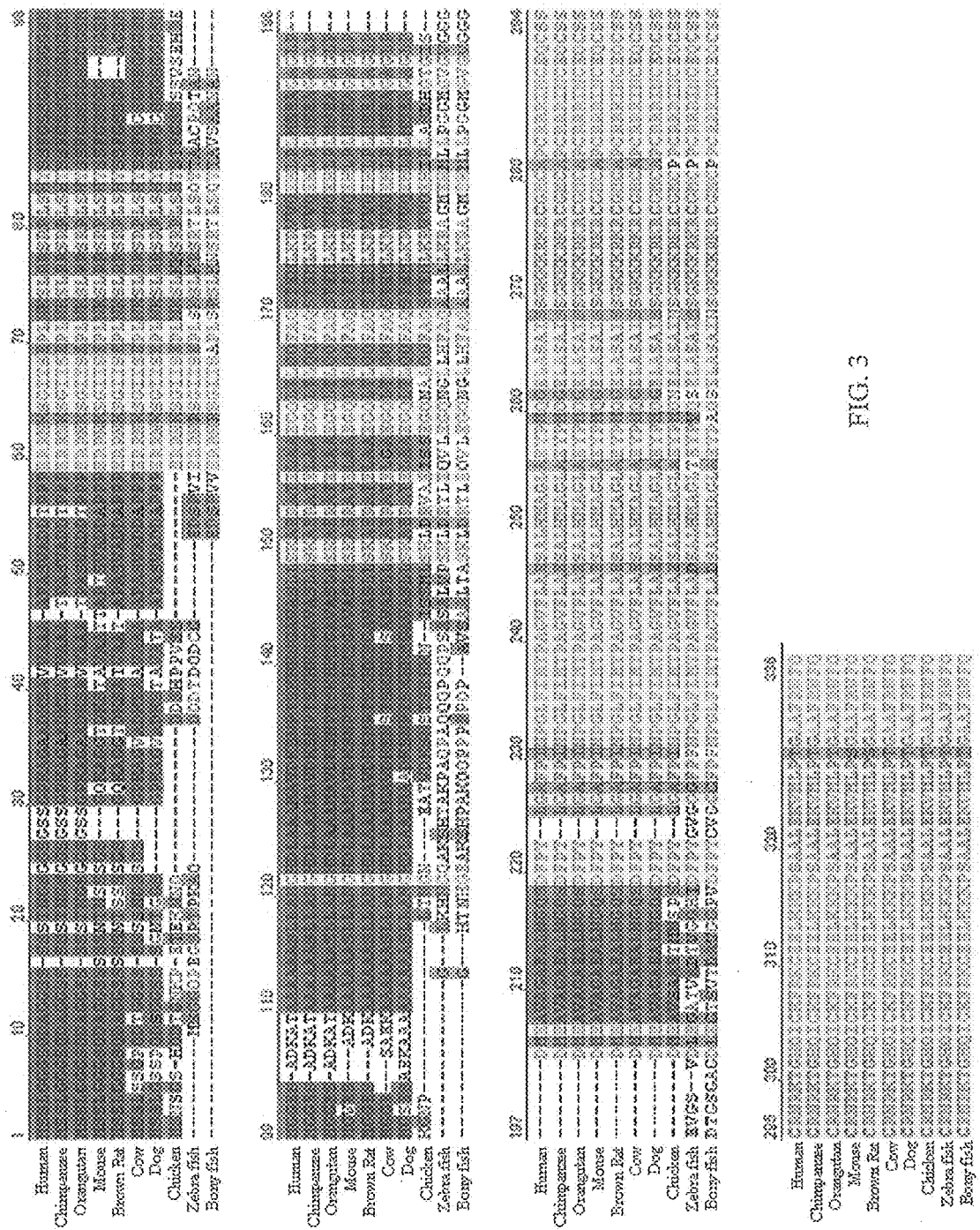
FIG. 3 shows the results obtained by comparing amino acid sequences of human Idbf obtained from a protein sequence database of the National Center for Biotechnology Information (NCBI) and Idbf-like proteins of an orangutan, a chimpanzee, a mouse, a rat, a dog, a cow, a chicken, a zebrafish and a bony fish using AlingX software.

Idbf was found by homology search of Idax, which was known as a patterner protein of Dishevelled (Dvl). FIG. 2 shows an alignment result between human Idbf and Idax, using a software, AlignX (Invitrogen). Human Idbf is composed of 332 anima acids, and shows 30.7% similarity with Idax. Identical and similar amino acids were indicated by yellow and green boxes, respectively, in FIG. 2. The carboxyl terminal region of these two proteins are very similar, including a double-repeat CXXCXXC motif, which has a potential to function as a metallic ion binding domain. A Dvl binding domain of Idax, which is composed of 13 amino acids, is also located on the carboxyl terminal region of both proteins (FIG. 2, asterisk). Idbf-like proteins were found in all kinds of vertebrates, excepting amphibians. The FIG. 3 shows an alignment result among the Idbf-like proteins of human (AAH24040), orangutan (CAH92226), chimpanzee (XP_517969), mouse (NP_598448), rat (NP_001007629), dog (XP_848437), cow (XP_580617), chicken (XP_414471), zebra fish (XP_686158) and bony fish (CAG00538), which were obtained from an protein sequence database of NCBI. The conserved and identical amino acids were indicated by sky-blue and yellow boxes, respectively, in FIG. 3.

2. An Expression Pattern of Idbf in Various Mouse Tissues

Muscle, pancreas, colon, intestine, bone, lung, and skin were isolated from an eleven-week old mouse. The organs were grinded in liquid nitrogen, and lysed in RIPA buffer. The lysates were subjected into immunoblotting analyses using anti-β-catenin (Santa Cruz), anti-Idbf (home-made), or anti-β-actin antibodies, and a horseradish peroxidase-conjugated secondary antibody. To produce anti-Idbf antibody, we cloned Idbf using cDNA clone (GenBank #BC017439, ATCC, Manassas, Va.) and the primers listed below.

Forward Primer:
5'-GGAATTCCATATGTCGAGCCTCGGCGGT-3'  (SEQ ID NO: 8)

Reverse Primer:
5'-CGCGGATCCTCACTGAAACCACCGGAA-3'  (SEQ ID NO: 9)

The 0.9 Kb PCR product was restricted using EcoRI and SalI, and subcloned into a pGEX4T1 vector (Amersham Bioscience) (pGEX4T1-Idbf). pGEX4T1 was introduced into E. Coli, and then the protein expression was induced by treating 1 mM IPTG. E. Coli was lysed by sonication, and then GST fused Idbf (GST-Idbf) was purified using Glutathione Resin (Clontech). One mg GST-Idbf in 1 ml Freund's complete adjuvant was injected to a rabbit to immunization, once per two weeks. After three times immunization, serum was obtained, and antibody was purified from it. Proteins were visualized by enhanced chemiluminescence (Amersham Bioscience). For RT-PCR analyses, grinded tissues were lysed using TRIzol reagent (Life Science), and total RNA was isolated as manufacturers' instruments. One μg of total RNA was subjected into reverse-transcription using 100 unit M-MLV reverse transcriptase (Invitrogen) to obtain cDNA pool. Five μg of cDNA pool was used as templet for Idbf and HPRT PCR with specific primers.

Figure 4A:
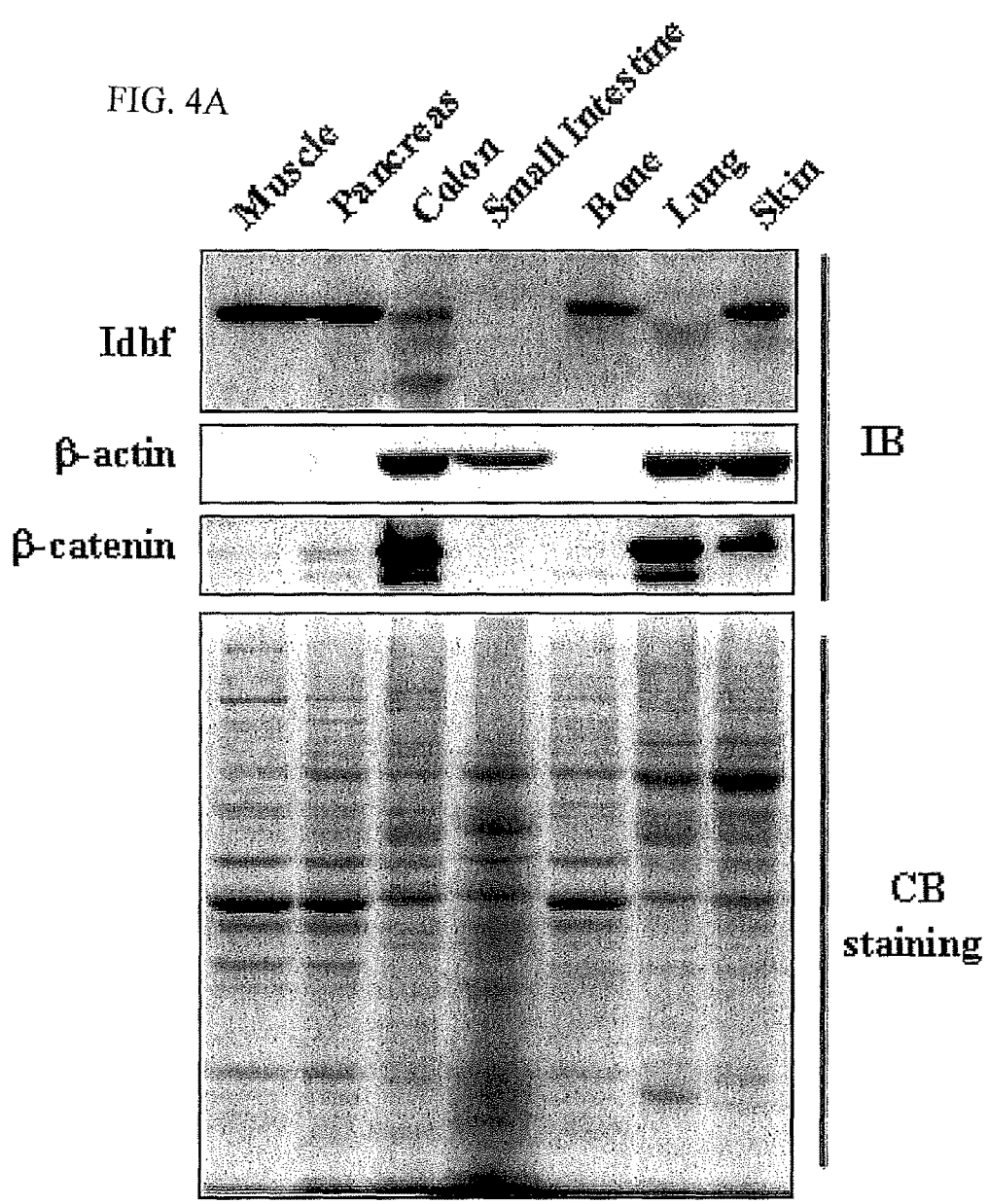
FIGS. 4A and 4B show the immunoblot assay results of Idbf proteins expressed in a muscle, a pancreas, large and small intestines, a bone, lungs and skin.
Figure 4B:
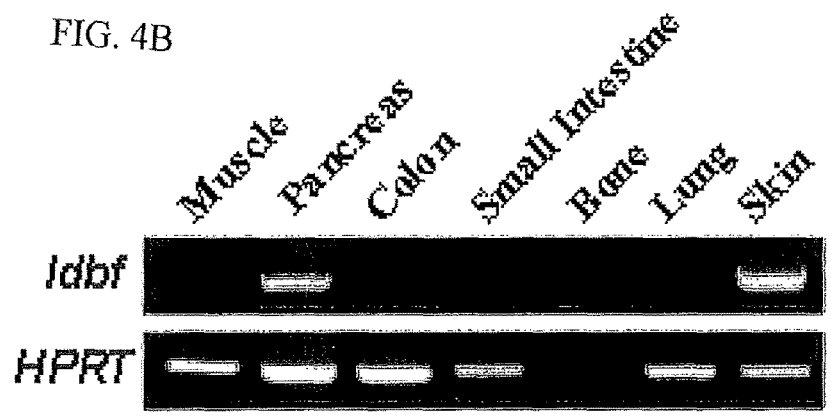

FIG. 4 shows the expression pattern of Idbf in various tissues, including muscle, pancreas, colon, intestine, bone, lung and skin. The upper panel of FIG. 4A shows the immunoblotting results with anti-β-catenin, anti-Idbf, and anti-β-actin antibodies. The lower panel of FIG. 4A shows the amounts of total proteins loaded on each lane, using Coomassie blue staining. FIG. 4B is a result of RT-PCR, which shows the levels of Idbf mRNA in each tissues. FIG. 4B revealed that the level of Idbf mRNA is relatively higher in muscle, pancreas, colon, skin, and bone than in other tissues.

3. Study of Idbf Cellular Function in Wnt/β-Catenin Pathway Using HEK293 Cells

The function of Idbf in Wnt/β-catenin pathway was investigated using HEK293 cells. Firstly, the protein level and transcriptional activity of β-catenin in Idbf overexpressed or knock-downed cells were monitored.

For subcloning of Idbf, PCR was done using Idbf cDNA clone (GenBank #BC017439, ATCC, Manassas, Va.) and primers listed below.

```
Forward Primer:                           (SEQ ID NO: 10)
5'-GCTCAGACTATGTCGAGCCTCGGCGGT-3'

Reverse Primer:                           (SEQ ID NO: 11)
5'-CGCGGATCCTCACTGAAACCACCGGAAGGC-3'
```

0.9 kb PCR product was restricted with XbaI and BamHI, and subcloned into a pcDNA3.1/myc His(−) vector (Invitrogen) (pcDNA3.1-Idbf-Myc). Idbf overexpression was performed by transfection of pcDNA3.1-Idbf-Myc into HEK293 cells using Lipofectamine plus reagent (Invitrogen) as the manufacturers' instruments.

Idbf knock-down was performed by transfection of Idbf siRNA into HEK293 cells using Lipofectamine plus reagent (Invitrogen) as the manufacturers' instruments. Idbf siRNA was synthesized using Silence™ siRNA Construction Kit (Ambion). To elevate the efficiency of knock-down, the mixture of two kinds of siRNAs, which are targeting different site of Idbf mRNA, were used.

```
Idbf siRNA
5'-UUGUAGGAAUCGAAAGACUUU-3'      (SEQ ID NO: 12)

5'-AGUCUUUCGAUUCCUACAAUU-3'      (SEQ ID NO: 13)

5'-GCAGUUUGCGCAGUCCACAUU-3'      (SEQ ID NO: 14)

5'-UGUGGACUGCGCAAACUGCUU-3'      (SEQ ID NO: 15)
```

For immunoblotting, cells were harvested, and lysed in RIPA buffer (50 mM Tris pH 7.5, 150 mM NaCl, 1 mM EDTA, and 1% Triton X-100). All chemicals were purchased from Sigma-Aldrich.

Figure 5B:
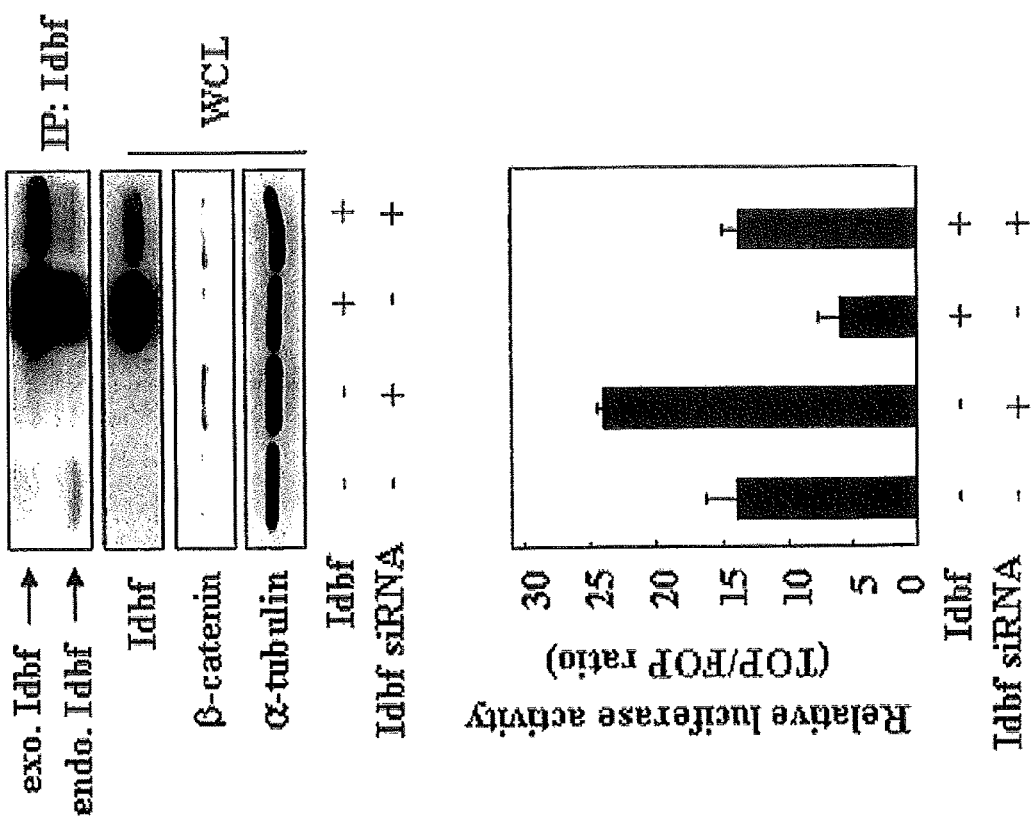
FIG. 5 is a diagram showing changes in protein amount and transcriptional activity of β-catenin according to overexpression of Idbf (FIG. 5A) or inhibition of Idbf expression (FIG. 5B).
Figure 5A:
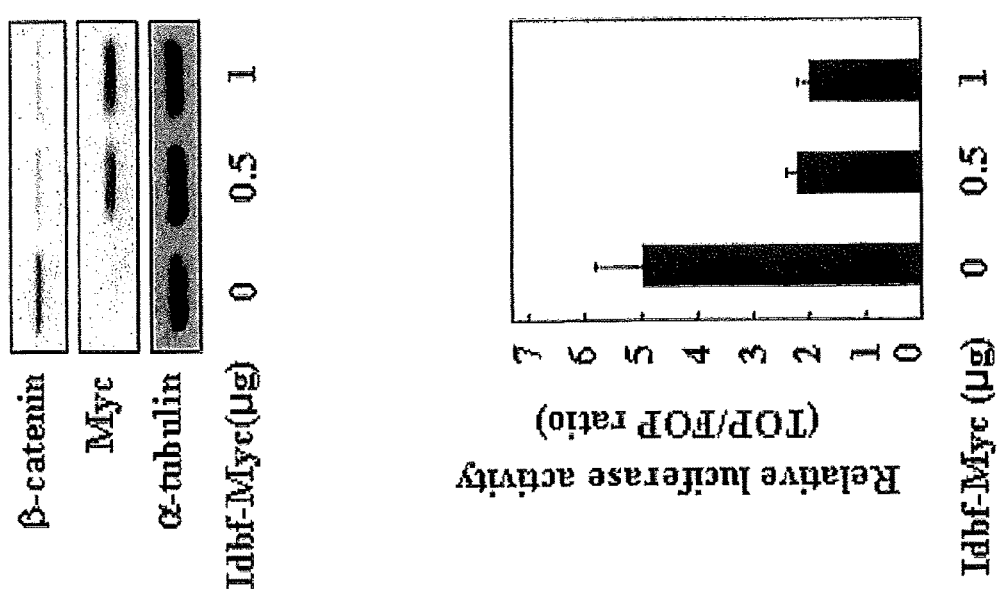
Figure 6:
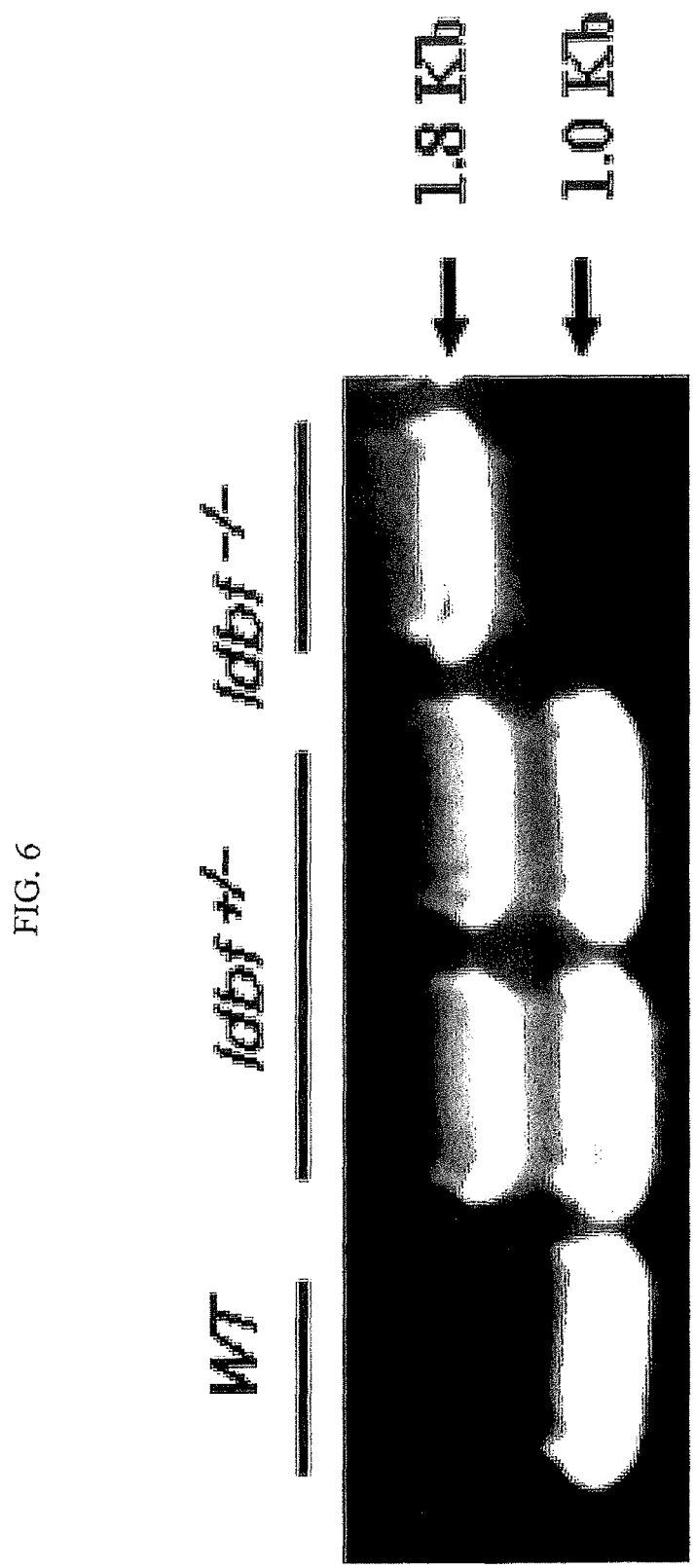
FIG. 6 shows the PCR results showing gene targeting in mice.
Figure 7:
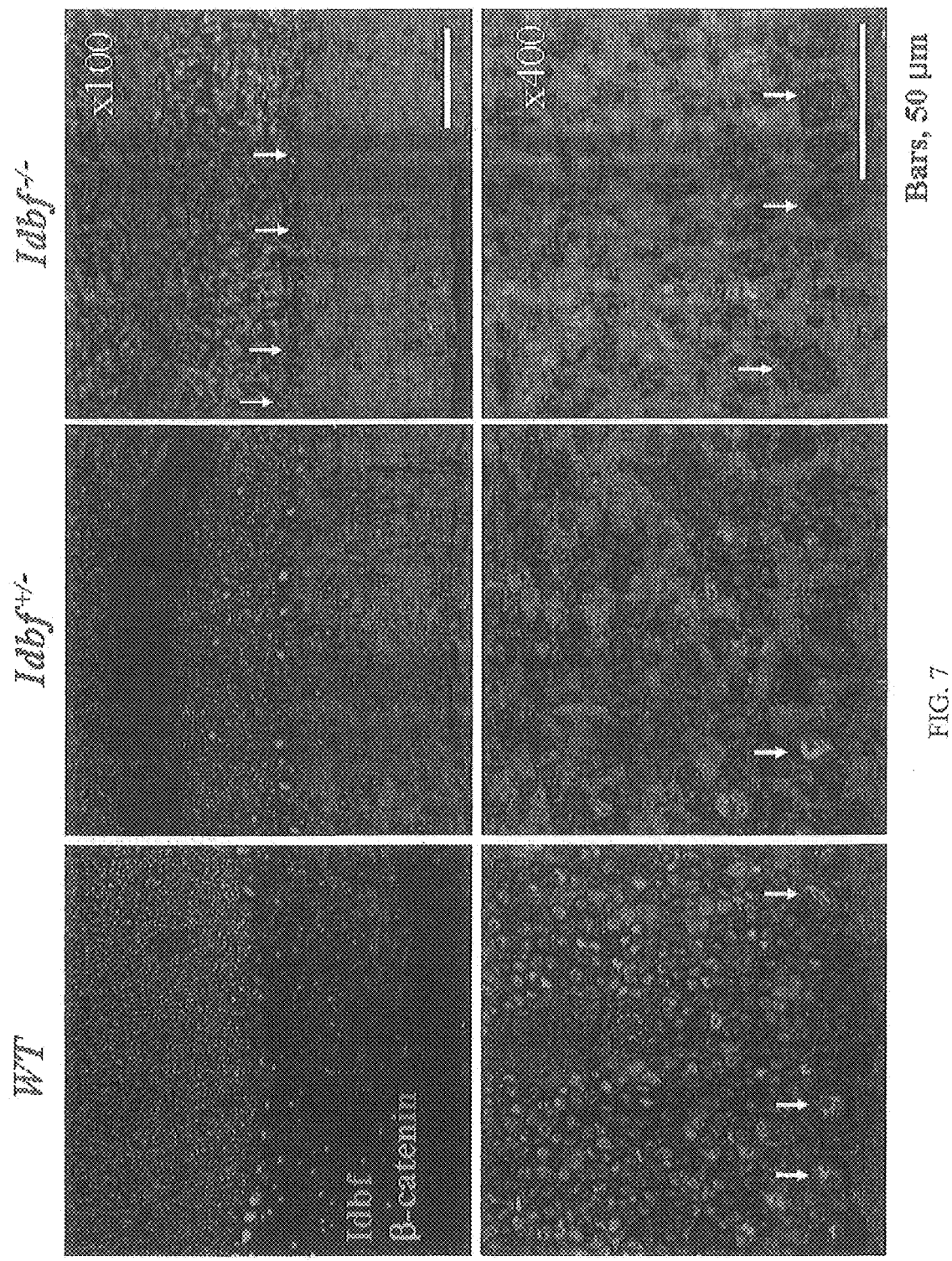
FIG. 7 shows the immunochemical assay results showing changes in expression levels of Idbf (green) and β-catenin (red) according to the knockout of the Idbf.

To detect proteins, whole cell lysates or immunoprecipitants were subjected into immunoblotting using anti-β-catenin, anti-Myc, or anti-α-tubulin antibodies. To monitor the transcriptional activity of β-catenin, 0.5 µg of pTOPFLASH or pFOPFLASH (kind gill from Dr. B. Vogelstein and Dr. K. Kinzler in Johns Hopkins Oncology Center, Baltimore, Md.) with 50 ng of pCMV-β-Gal was transfected into HEK293 cells. The luciferease activities, which indicate the transcriptional activity of β-catenin, were normalized by β-galactosidase activities, which show the efficiency of transfection. FIG. 5 shows that the protein level of β-catenin and its transcriptional activity were reduced by Idbf overexpression (FIG. 5A). Oppositely, the protein level of β-catenin and its transcriptional activity were increased by Idbf knock-down (FIG. 5B). Error bars in FIG. 5 indicates standard deviation. WCL and IP are abbreviations of whole cell lysate and immunoprecipitation, respectively.

4. Study of Idbf In Vivo Function Using Idbf Knock-Out Mice

To study the in viva function of Idbf, Idbf knock-out mice were generated using homologous recombination. Idbf is located on chromosome 18 of mouse and is composed of three Exons.

Firstly, to produce pPNT-Idbf vector, which was used for homologous recombination, two fragments of Idbf genomic DNA (a 7 kb NotI-XhoI restricted fragment of Exon 2 upstream, and a 2.5 kb XhoI-BamHI restricted fragment of Exon 2 downstream) were restricted from mouse genome, and then subcloned into a pPNT vector (Tybulewicz et al., 1991) (pPNT-Idbf)

Idbf knock-out embryonic stem cells (ESCs) were produced by introducing pPNT-Idbf linearized by EcoRI into CJ7 ESC, and replacing Exon 2, which includes starting codon ATG, with AGK-Neo. Knock-out ESCs introduced into a blastocyst of C57BL/6 mouse to obtain germ-line transmitted chimeras, and the chimeras mated with a wild-type C57BL/6 mouse to produce first generation of knock-out mice. Knock-out was confirmed by PCR using genomic DNA isolated from mouse tails and primers listed below.

```
Forward Primer:
5'-CAGAGTAAAGACATTTCCACGT-3'       (SEQ ID NO: 16)

Reverse Primer:
5'-GCTCTGACTTTTAGGGCAGT-3'         (SEQ ID NO: 17)
```

Idbf knock-out was also confirmed by immunohistochemical analyses of cerebellum in knock-out mice. The brain sections of eleven-week-old Idbf$^{+/+}$, Idbf$^{+/-}$, and Idbf$^{-/-}$ mice were fixed by paraformaldehyde (4%), and permeabilized by saponin (0.2%). The sections were incubated with anti-Idbf and anti-β-catenin antibodies, and then incubated with Alexafluor 488 or Alexafluor 555 conjugated secondary antibodies. While Idbf expressing cells (green) were observed in the granular cell layer of mice's cerebellum, they disappeared in the brain of knock-out mice. With disappearance of Idbf, the expressing level of β-catenin and the number of β-catenin expressing cells were increased (red). Green signals were also observed in Purkinje cells. The signals from Purkinje cells seem to be nonspecific signals by anti-Idbf antibody, because they appeared regardless of whether or not Idbf was knock-outed.

Figure 9A:
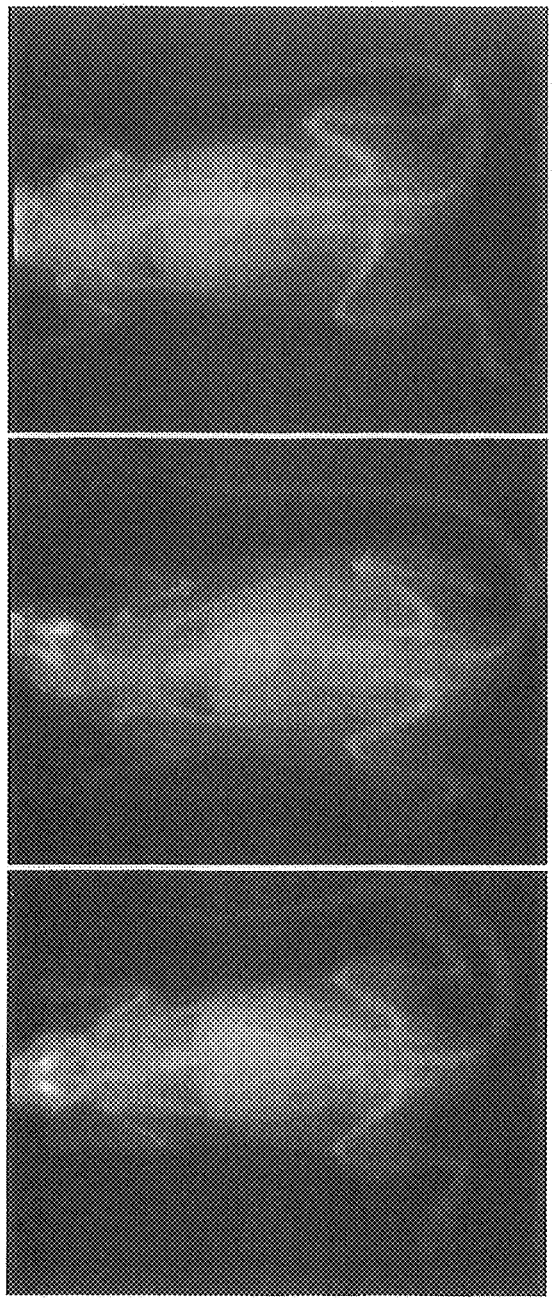
FIGS. 9A and 9B show X-ray images of representative genetic traits showing changes in femoral bone densities and femoral lengths of mice according to the knockout of the Idbf.
Figure 9B:
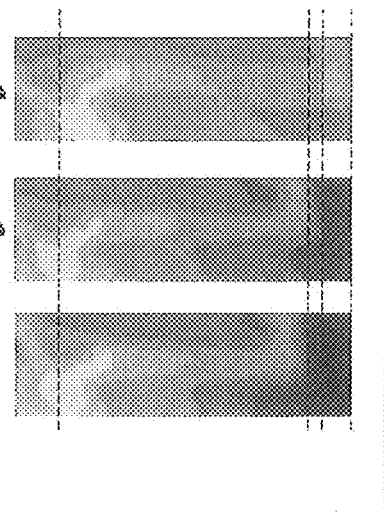

The average weight of Idbf$^{-/-}$ mice increased by 7.6% and 8.0%, compared with Idbf$^{+/+}$ and Idbf$^{+/-}$ mice, respectively (FIG. 8A). To investigate the function of Idbf in bone, bone mineral densities (BMDs) of wild-type and knock-out mice were monitored using a bone densitometry, PIXImus II (GE Healthcare). To remove variations of BMD by female hormones, BMD monitorings were performed only for male mice. The average BMDs of Idbf$^{-/-}$ mice increased by 8.9%, compared with Idbf$^{+/+}$ and Idbf$^{+/-}$ mice (FIG. 8B). In case of femurs, the difference of average BMDs was more significant: the average BMD of Ibdf$^{-/-}$ mice increased by 11.4% and 20.0%, compared with Idbf$^{+/+}$ and Idbf$^{+/-}$ mice, respectively (FIG. 8C). Representative X-ray images were shown in FIG. 9. From these images, the length of femurs was measured, and the aspect of result was revealed as similar with the case of BMD (FIG. 8D).

Figure 10A:
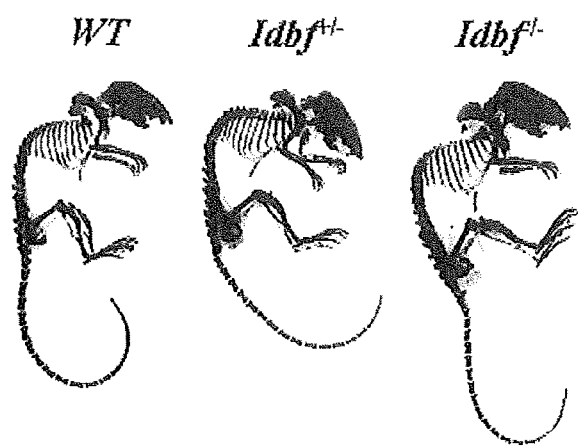
FIG. 10 is a photograph showing craniums and winged scapulas (10A) and shinbones (10B) being increased in size and compact bones (10C) being increased in length and thickness according to the knockout of the Idbf.
Figure 10B:
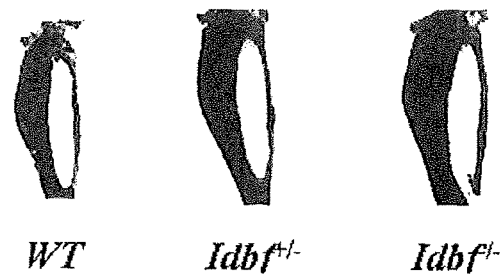
Figure 10C:
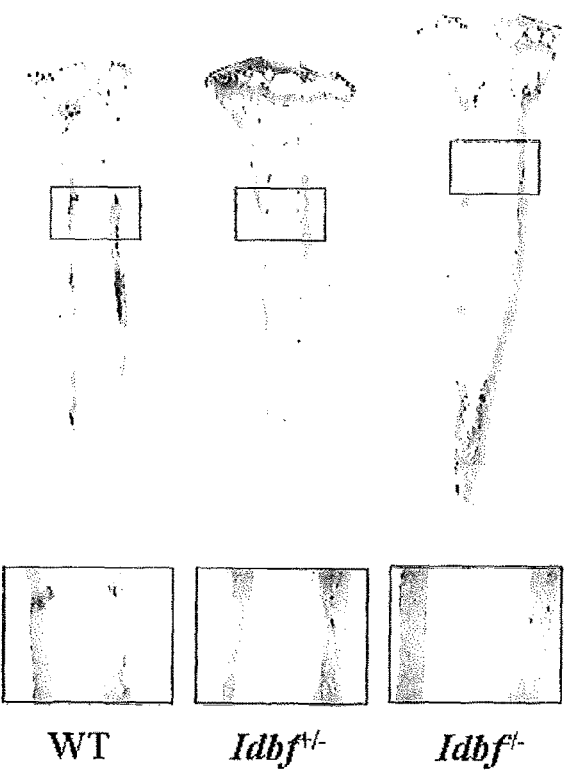

The size of skull and wing of Idbf$^{-/-}$ mice also increased compared with Idbf$^{+/+}$ and Idbf$^{+/-}$ mice (FIG. 10A). In addition, tibiae of Idbf$^{-/-}$ mice were thicker and longer than those of wild-type mice (FIG. 10B). The sections of femurs showed that the length and thickness of bone increased (FIG. 10C)

Immunohistochemical analyses of femoral epiphysis were performed. Femurs of eleven-week-old mice were fixed in 4% paraformaldehyde. Fixed bones were decalcificated in 10 mM EDTA, and then embedded into paraffin blocks. The paraffin blocks were sectioned using microtome, and the sections were stained by hematoxylin and eosin solutions (H&E staining). To detect specific proteins from the sections, the sections were permeabilized with 0.2% saponin, and then incubated in 5% BSA solution for blocking. After blocking, the sections were incubated with primary antibody solution overnight, in a humidity chamber. The concentrations of primary antibodies were listed: anti-Idbf (1:20), anti-β-catenin (home-maed; 1:100), anti-Ki67 (Abeam; 1:100), and anti-Fgf18 (Santa Cruz; 1:50). For diaminobenzidine (DAB) staining, sections were incubated with biotylated secondary antibody (Dako; 1:200) and avidin conjugated HRP for 1 hour, at room temperature, and then incubated with DAB solution to visualize proteins. After visualization, the sections were counterstained with hematoxylin solution, DAB-stained slides were observed using ECLIPSE TE2000-U microscope (Nikon). For fluorescence staining, sections were incubated with Alex Fluor 488 or Alex Fluor 555 conjugated secondary antibodies (Molecular Probes; 1:200), and then counterstained with DAPI (Boehringer Mannheim). The stained sections were fixed with Gel/Mount media (Forster City, Calif.), and then visualized with lasers with 488 nm (for Alexa Fluor 488), or 543 nm (for Alexa Fluor 555) wavelength, using LSM510META (Carl Zeiss, Germany).

Figure 11:
FIG. 11 shows the histological assay results of femoral epiphyses in which cartilage cells growing in bone plates of mice can be observed.

The histological analyses of femoral epiphysis shows that more chondrocytes exist in the growth plate of Idbf$^-$ mice than in those of Idbf$^{+/+}$ and Idbf$^{+/-}$ mice (FIG. 11), Purple and pink areas in FIG. 11 indicate nucleus and cytosol, respectively. Chondrocytes in the growth plate of Idbf$^-$ mice showed huge nucleus, and formed columnar shapes (FIG. 11, arrows). Oppositely, chonrocytes in the growth plate of Idbf–/31 mice showed small nucleus, and were irregularly distributed (FIG. 11). Those of Idbf$^{+/-}$ mice showed intermediated status.

Figure 12:
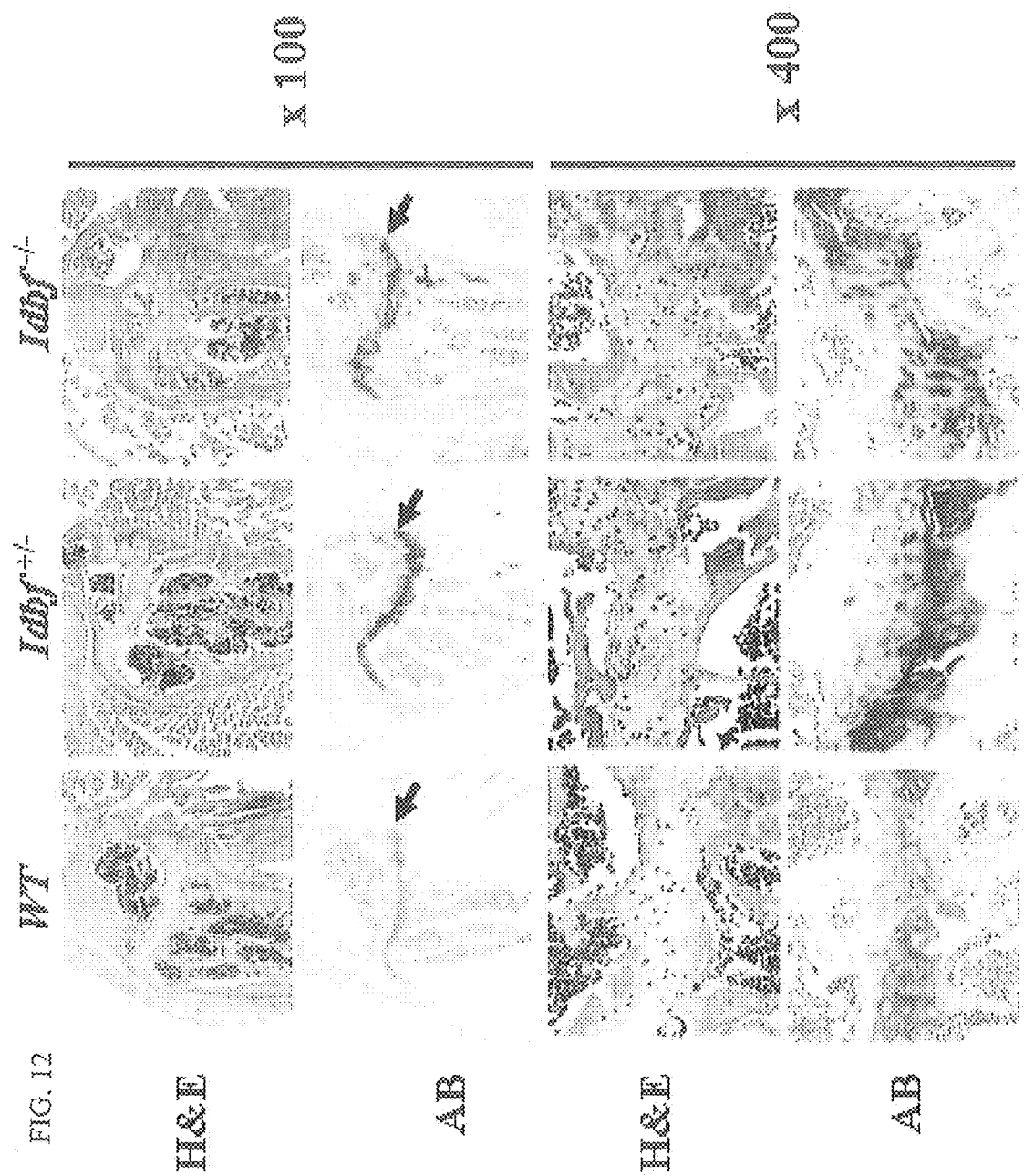
FIG. 12 shows the Alcian blue (AB) staining results of cartilage cells growing at the distal ends of mouse humeri.

Similar result was observed in humeri of Idbf knock-out mice. The humeri were sectioned, and the sections were stained by H&E and Alcian Blue (AB) stainings. AB staining visualize chondrocytes as blue color (FIG. 12).

Figure 13:
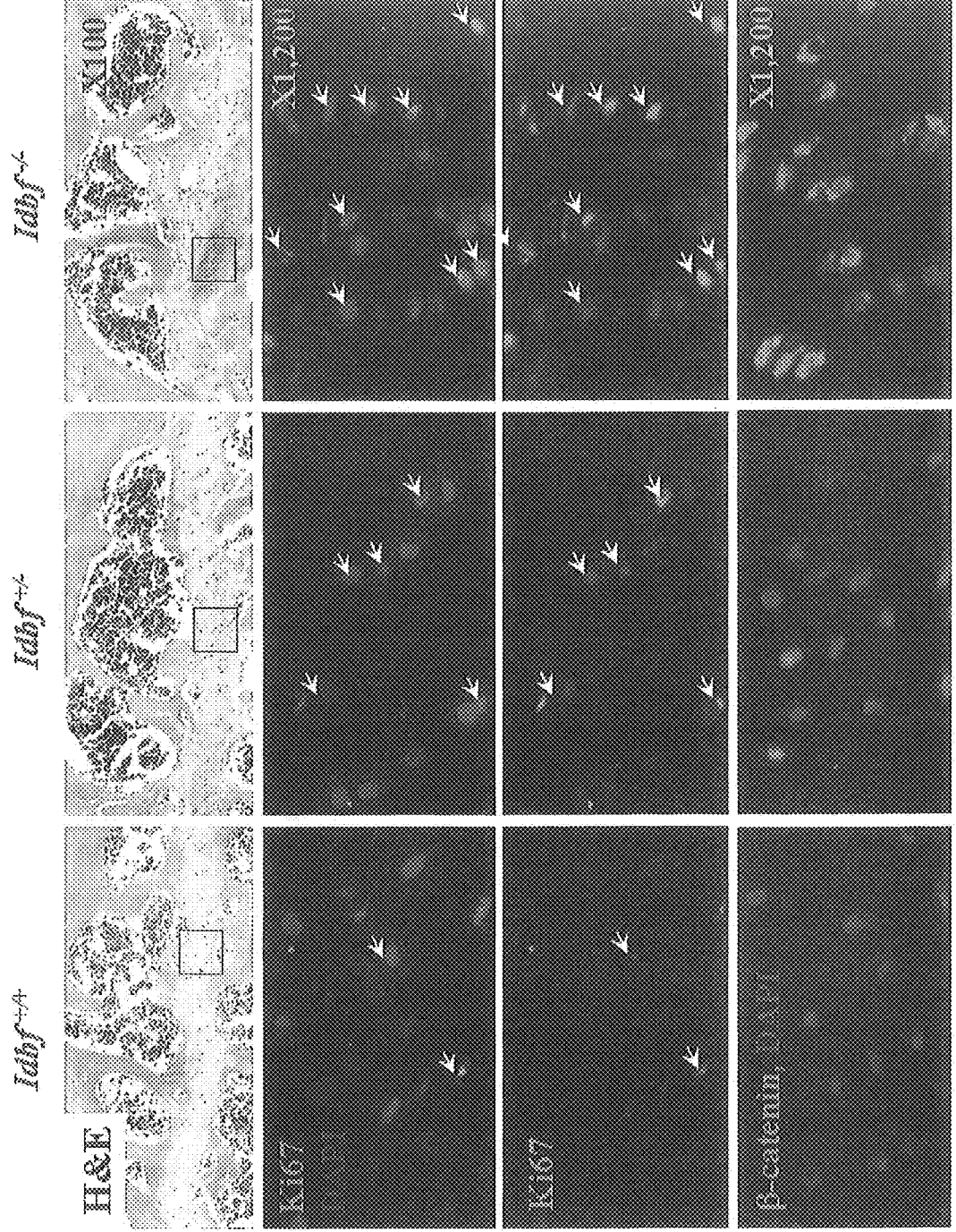
FIG. 13 shows the histostaining and immunofluorescent staining results of cartilage cells growing in mouse bone plates.

The panels in the middle of FIG. 13 shows a staining result with anti-Ki67 antibody. Expression of Ki67 indicates the cell is proliferating, and the staining result shows that the number of proliferating chondrocytes in a growth plate increased in Idbf$^-$ mice.

Figure 14:
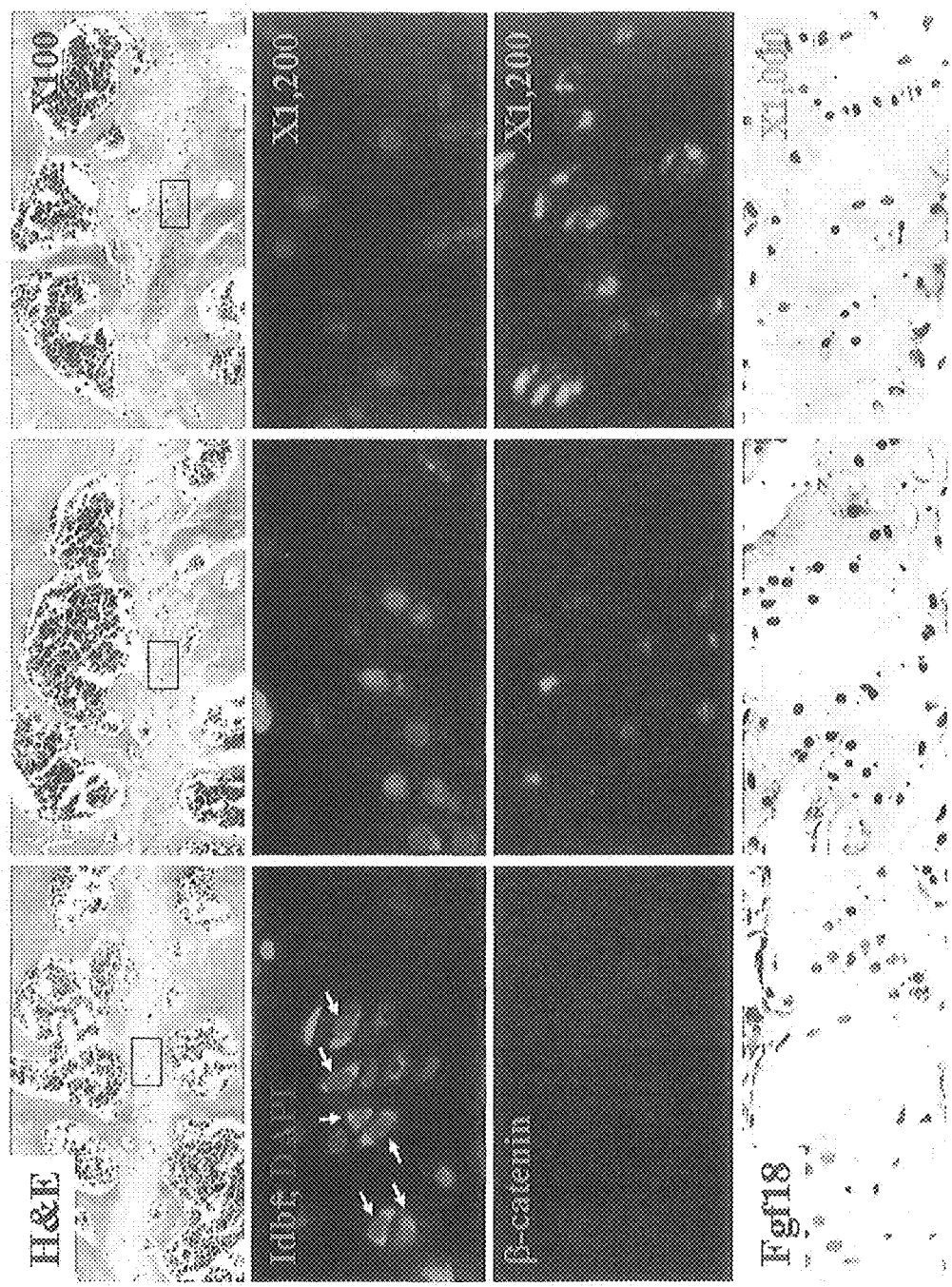
FIG. 14 shows the immunofluorescent staining results showing changes in expression levels of Idbf, β-catenin and Fgf18 in cartilage cells of the mouse bone plates according to the knockout of the Idbf.
Figure 15:
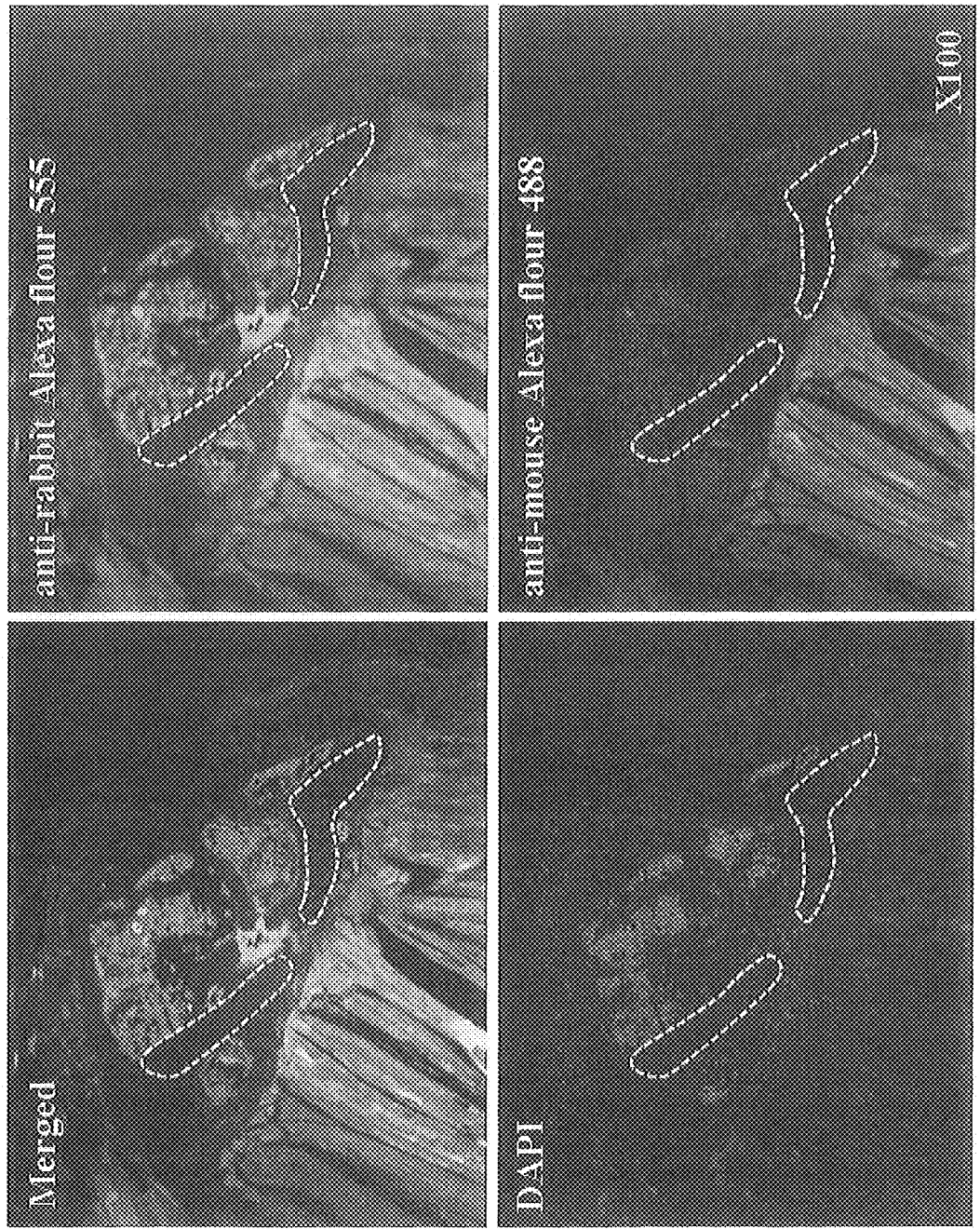
FIG. 15 shows the immunofluorescent staining results showing effects of the Idbf knockout on growth of bone plates.

Immunofluorescence staining of Idbf showed that Idbf is expressing in chondrocytes of growth plates, and the expression of Idbf reduced and abolished in those of Idbf$^{+/-}$ and Idbf$^-$ mice (FIG. 14), β-catenin in chondrocytes increased with decrease of Idbf in Idbf$^{+/-}$ and Idbf$^-$ mice (FIG. 14). While compact bone showed sever autofluorescence, such non-specific signals were not observed in the growth plate, when it stained without primary antibodies (FIG. 15). Idbf knock-out resulted in the activation of Wnt/β-catenin signaling, which is evidenced by increment of a target gene of Wnt/β-catenin pathway, Fgf18, in chondrocytes of Idbf$^-$ mouse growth plates (FIG. 14). Overall, promotion of bone formation in Idbf knock-out mice is caused by abnormal activation of Wnt/β-catenin signaling in the chondrocytes of growth plates.

5. Function of Idbf as a Negative Feedback Regulator of Wnt/Θ/Catenin Pathway and Osteogenic Differentiation of Osteoblast Cells To investigate the mechanism of BMD increment in Idbf knock-out mice, a pre-osteoblast cell-line, MC3T3E1 was used. MC3T3E1 cells are differentiated into osteocytes, when they are grown in media containing ascorbic acid and inorganic phosphates.

Figure 16:
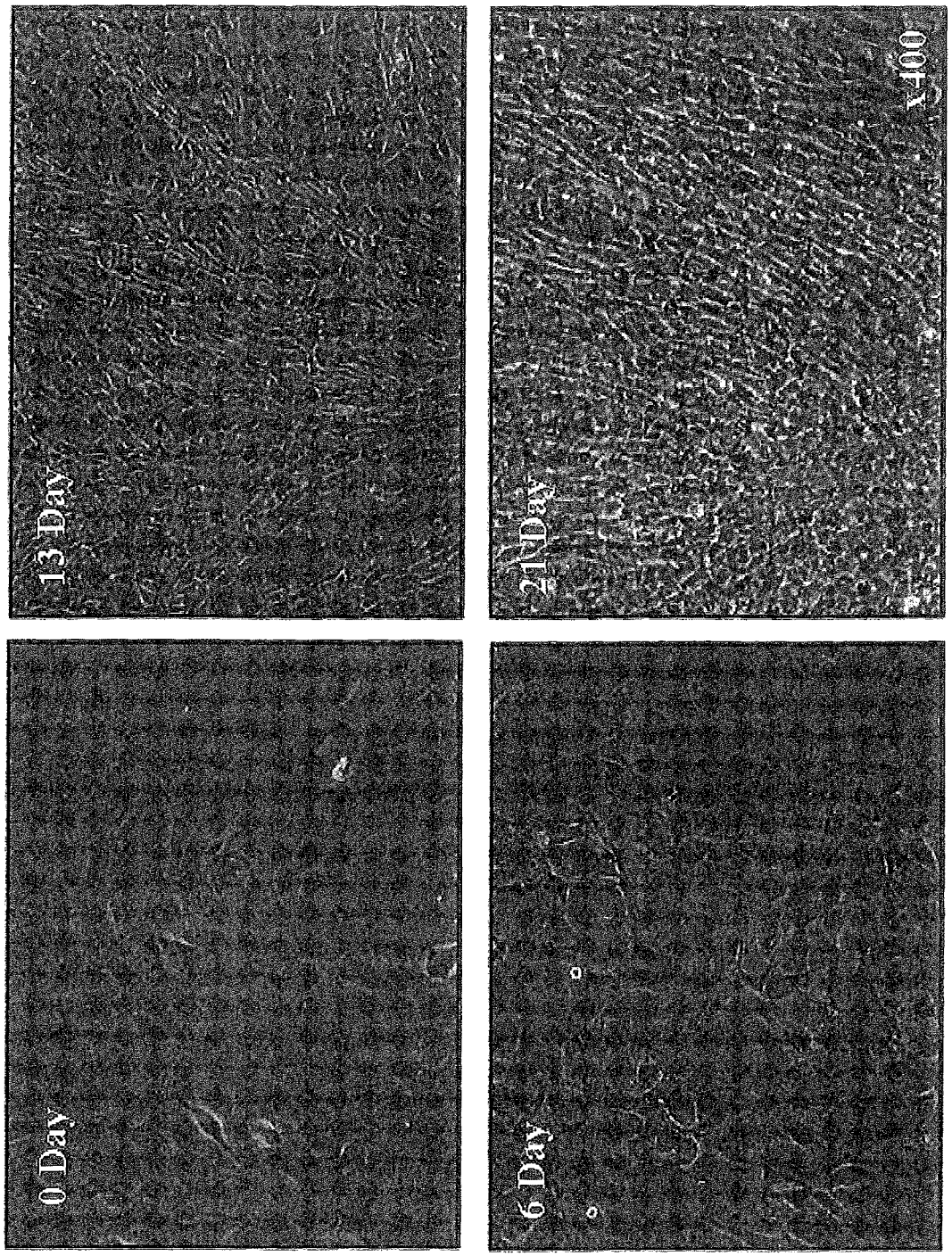
FIG. 16 is a photograph showing changes in cell shapes according to induced cell differentiation of an osteoblast cell line, MC3T3E1.

MC3T3E1 cells were differentiated for 0, 6, 13, or 21 days in α-MEM media containing 50 mg/l ascorbic acid and 10 mM Θ-glycerol-phosphate. The morphology of cells was observed using ECLIPSE TE2000-U microscope. MC3T3E1 cells, which were incubated in differentiation media, showed compact fibril morphology because of accumulation of extracellular matrix, which was screted from differentiating pre-osteoblast cells (FIG. 16).

Figure 17A:
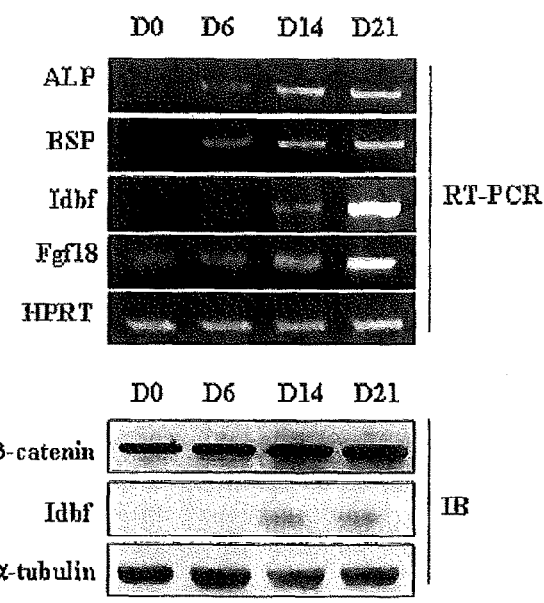
FIGS. 17A-17C show a correlation between differentiation in MC3T3E1 osteoblast and expressions of Idbf, β-catenin, and Fgf18.
Figure 17B:

To monitor the expression of Idbf, β-catenin, and Fgf18 in differentiating pre-osteoblast cells, the cells differentiated 0, 6, 14, or 21 days were harvested and the total RNAs and total proteins were prepared. RT-PCR analyses were performed using total RNAs to detect the mRNA amounts of ALP, BSP, Idbf, Fgf18 and HPRT. Total proteins were subjected into immunoblotting analyses to monitor the amounts of β-catenin, Idbf, and α-tubulin. The differentation of osteoblast cells were confirmed by mRNA increment of osteogenic differentiation markers, ALP, BSP. (FIG. 17A). The amount of β-catenin increased with osteoblast differentiation (FIG. 17A). Interestingly, the mRNA and protein amounts of Idbf increased with osteoblast differentiation (FIG. 17B).

Figure 17C:
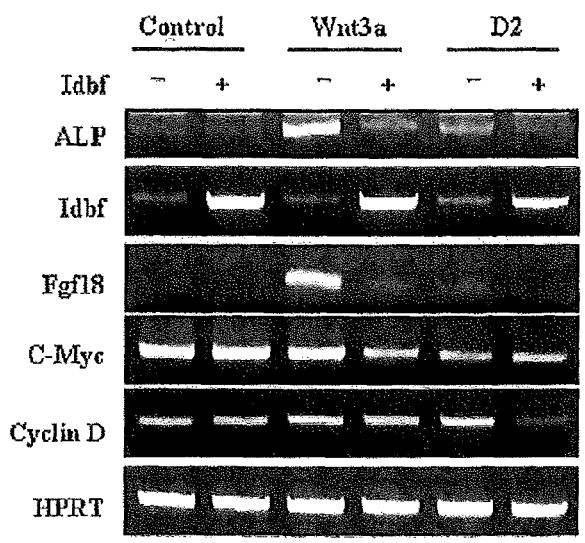

Idbf was overexpressed in MC3T3E1 cells to investigate the function of Idbf in Wnt/β-catenin pathway and osteoblast differentiation. MC3T3E1 cells were transfected with pcDNA3.1 or pcDNA3.1-Idbf-Myc, and then transfected cells were incubated in α-MEM media containing 100 ng/ml Wnt3a for 12 hours or in α-MEM containing 50 mg/l ascorbic acid and 10 mM 3-glycerol-phosphate for 2 days. Wnt3a treatment results in mRNA increments of ALP and Fgf18, which were more significant than ascorbic acid and β-glycerol-phosphate treatment (FIG. 17C). Idbf overexpression suppressed increment of ALP and Fgf18 mRNA, which induced by Wnt3a or ascorbic acid and β-glycerol-phosphate treatment (FIG. 17C). However, the common target genes of Wnt/β-catenin pathway, cyclin D and c-myc were not regulated by Wnt3a or ascorbic acid and β-glycerol-phosphate treatment (FIG. 17C). This result shows the specificity of Wnt/β-catenin pathway for regulation of osteogenic differentiation markers in osteoblas cells (FIG. 17C).

6. The importance of Idbf-Dvl-1 Binding for Regulation of Wnt/β-Catenin Pathway and Osteoblast Differentiation To investigate the importance of Idbf-Dvl-1 binding in Idbf function, a mutant of Idbf, in which Dvl binding minimal peptide (DBMP; RKTGHQICKFRKC, SEQ ID NO: 4) was removed, was produced (pcDNA3.1-Idbf-ΔDBMP-Myc).

To produce DBMP deleted Idbf, pcDNA3.1-Idbf was subjected into PCR using primers listed below.

|  | forward primer | Reverse primer |
|---|---|---|
| Up stream | 5'-GCTCTAGACTATGTCG AGCCTCGGCGGT-3' (SEQ ID NO: 18) | 5'-TGAGTTCCTCATTCCTAC AACTGCT-3' (SEQ ID NO: 19) |
| Down stream | 5'-TTGTAG-GAATGAGGA ACTCAAAAAG-3' (SEQ ID NO: 20) | 5'-CGCGGATCCTCACTGAAA CCACCGGAA-GGC-3' (SEQ ID NO: 21) |

Two PCR products were mixed, and the mixture subjected into PCR again using upstream forward primer (SEQ ID NO: 18) and downstream reverse primer (SEQ ID NO: 21). The PCR product was subcloned into pcDNA3.1/myc His(−) vector. Removal of DBMP was confirmed by DNA sequencing.

Figure 18A:
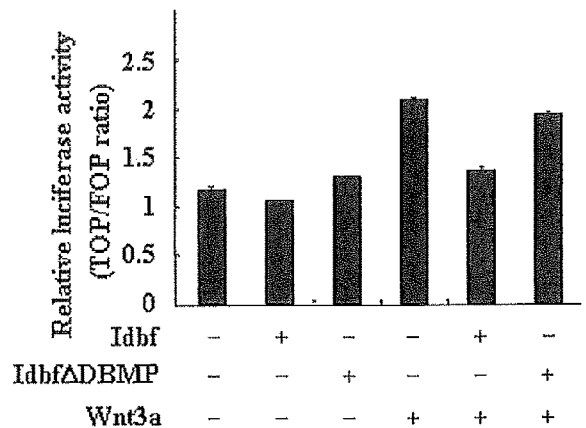
FIGS. 18A-18D show an Idbf-Dvl-1 interaction in MC3T3E1 osteoblast and effects of the interaction on a Wnt/β-catenin signaling pathway and differentiation.

For reporter assay, pTOPFLASH or pFOPFLASH was transfected with pCS2-Dvl-1 and pCMV-β-Gal into HEK293 cells. The transfected cells were incubated in α-MEM with or without 100 ng/ml Wnt3a for 16 hours, and then lysed in Lysis Buffer (Promega). The cell lysates were mixed with Luciferase Substrate (Promega) to monitor the luciferase activities. The luciferase activities were normalized by β-galactosidase activity, which shows transfection efficiency. Error bars in FIG. 18A indicates standard deviations of three independent experimental results.

Figure 18B:
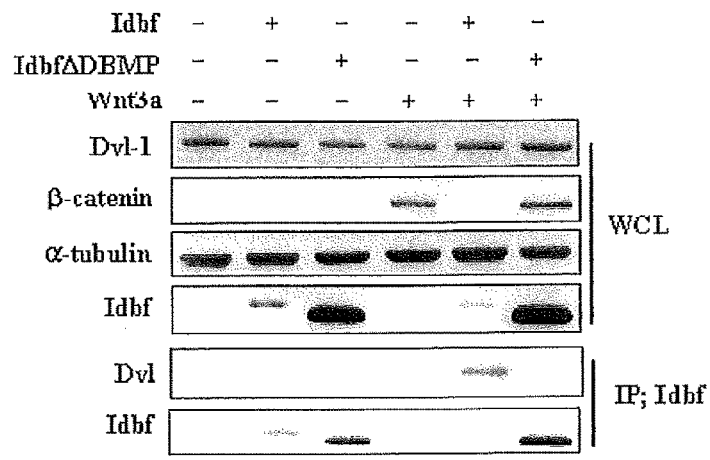
Figure 18C:
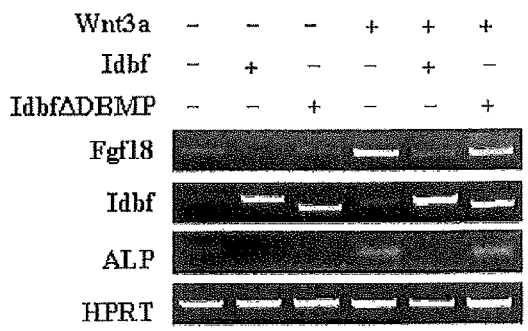

To monitor Idbf-Dvl-1 binding, cell lysates were subjected into immunoprecipitation using anti-Idbf antibody. Whole cell lysates were subjected into immunoblotting to detect the amounts of proteins, including β-catenin, α-tubulin, and Dvl-1. The result revealed that Idbf binds to Dvl-1 in Wnt3a-dependent manner (FIG. 18B). However, Idbf-ΔDBMP did not bind to Dvl-1 regardless of whether or not Wnt3a existed (FIG. 18B). Idbf-ΔDBMP overexpression did not reduce the amount of Fgf18 and ALP mRNA (FIG. 18C). These result shows that Idbf-Dvl-1 binding is important for Idbf to regulate osteoblast differentiation.

To investigate the importance of Fgf18 in regulation of osteoblast differentiation by Wnt/β-catenin pathway, ds-siRNA of Fgf18 (5 nM) was introduced into MC3T3E1 cells. To elevate knock-down efficiency, two kinds of Fgf18 siRNA, which are targeting different site of Fgf18 mRNA, was mixed. The sequences of siRNAs are listed below.

```
Fgf18 siRNA
5'-UGUGGACUUCCGCAUCCACUU-3'       (SEQ ID NO: 22)

5'-GTGGAUGCGGAAGTCCACAUU-3'       (SEQ ID NO: 23)

5'-GCAGCUGCGCUU-GUACCAGUU-3'      (SEQ ID NO: 24)

5'-CUGGUACAAGCGCAGCTGCUU-3'       (SEQ ID NO: 25)
```

Figure 18D:
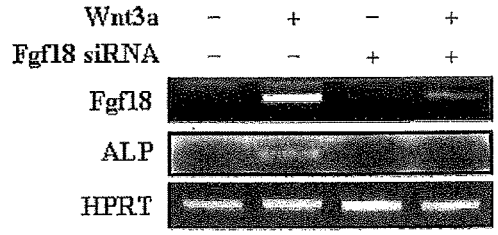

Twelve hours before harvest, 100 ng/ml Wnt3a was treated to the cells. Total RNAs were isolated from harvested cells using TRIzol. Isolated total RNAs were subjected into RT-PCR to detect the amounts of ALP, Fgf18, and HPRT mRNA. FIG. 18D shows Fgf18 knock-down results in reduction of Fgf18 mRNA, which was induced by Wnt3a treatment. This result shows that Fgf18 mediates between Wnt/β-catenin pathway and osteoblast differentiation.

Figure 19:
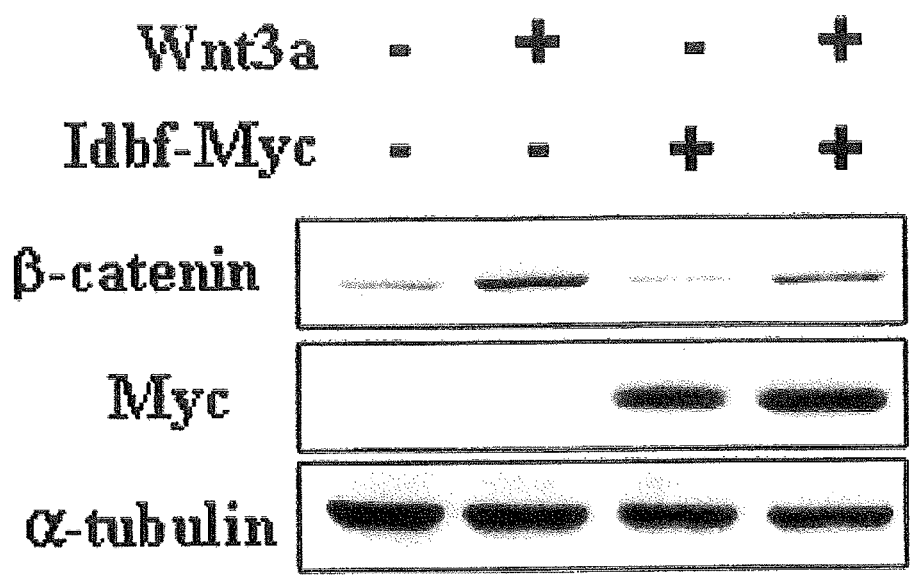
FIG. 19 shows effects of Idbf on activation of Wnt3a in a kidney-derived cell HEK.
Figure 19:
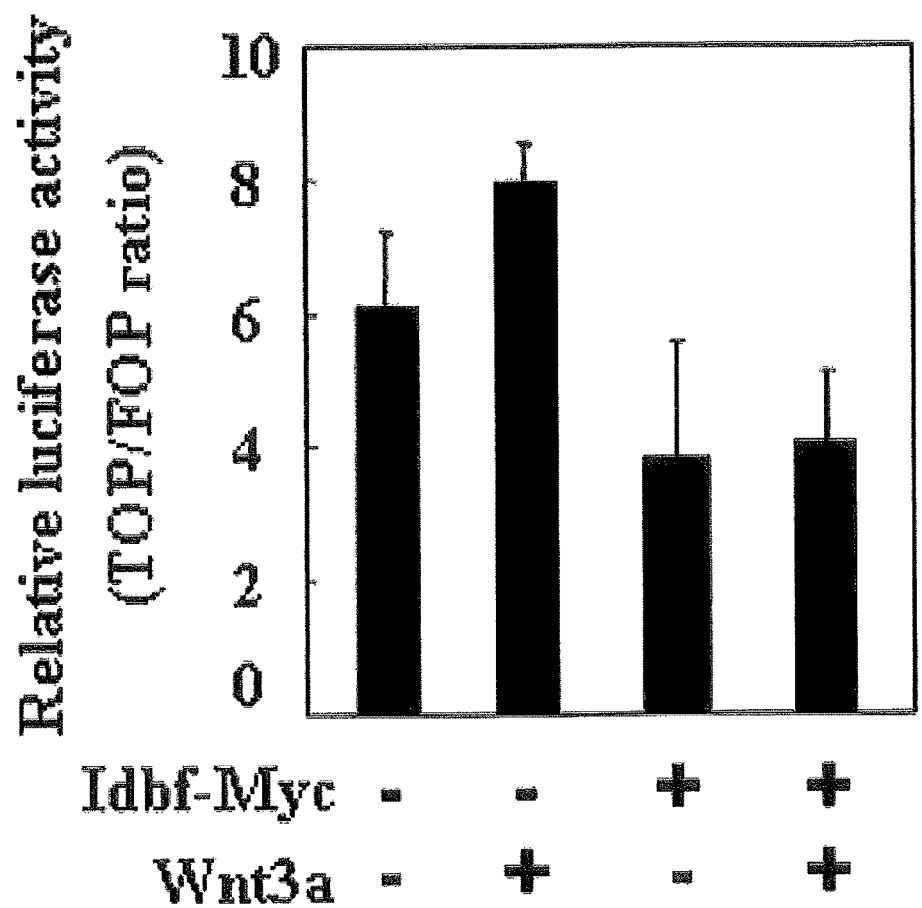
Figure 20:
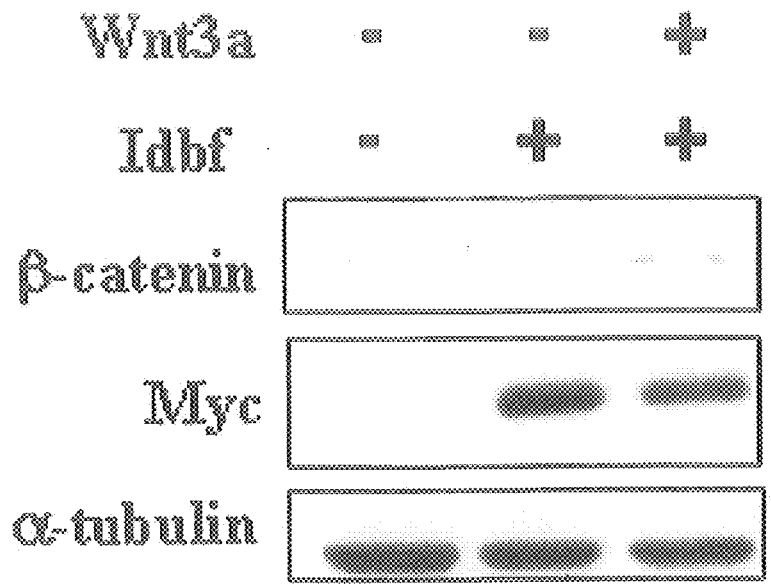
FIG. 20 shows effects of Wnt3a on Idbf-Dvl-1 interaction in a HEK 293 cell.
Figure 20:
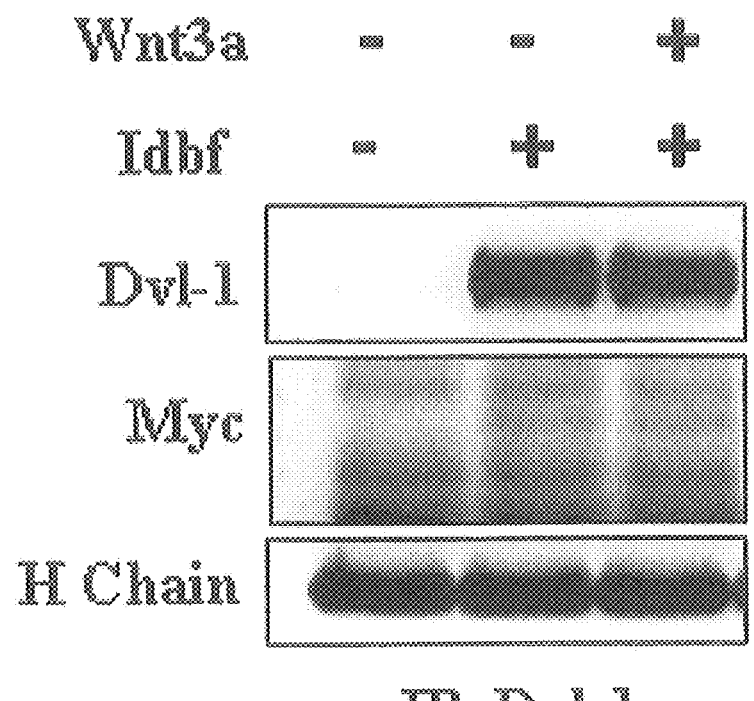

Function of Idbf in Wnt/β-catenin pathway was also studied in HEK293 cells, which is a established human embryonic kidney cell-line. HEK293 cells were transfected with 0.5 μg pcDNA3.1 or pcDNA3.1-Idbf-Myc. For reporter assay, 0.5 μg pTOPFLASH or pFOPFLASH with 50 ng pCMV-β-Gal was co-transfected. The transfeced cells were incubated in α-MEM with or without 100 ng/ml Wnt3a for 12 hours. FIG. 19 shows that the effect of Wnt3a treatment or Idbf overexpression was very marginal in HEK293 cells. The enhancement of Idbf-Dvl-1 binding by Wnt3a treatment was also not observed (FIG. 20). Overexpression of Idbf-ΔDBMP showed no effects on Wnt/β-catenin pathway in HEK293 cells, as observed in MC3T3E1 cells.

Overall, regulation of Wnt/β-catenin pathway by Idbf is followed by Fgf18 regulation, which results in control of osteoblast differentiation. For the function of Idbf, Idbf-Dvl-1 binding is required.

7. Introduction of PTD Conjugated DBMP (PTD-DBMP) into Cells and the Effect of PTD-DBMP on Wnt/β-Catenin Pathway To investigate the function of DBMP (RKTGHQICK-FRKC, SEQ ID NO: 4), two kinds of PTD (RRRRRRRR (SEQ ID NO: 28), YGKKRRQRRR (SEQ ID NO: 29)), and glycine linker (GGGG) were conjugated on amino terminal region of DBMP, and fluorescence dye (FITC) was conjugated on carboxyl terminal region of the peptide, as listed below.

PolyR-DBMP: RRRRRRRRGGGGRKTGHQICK-FRKCK (SEQ ID NO: 26)-(FITC)

HIV(Tat)-DBMP: YGRKKRRQRRRGGGGRKTGH-QICKFRKCK (SEQ ID NO: 27)-(FITC)

To confirm the introduction of two PTD-DBMP into cells, HEK293 cells were seeded and incubated on gelatin-coated glasses for one day, and then 1 μM or 4 μM peptide were treated on the cells. After 3 hours, the cells were washed with PBS, and then fixed using fixative solution (99% methanol and 1% formaldehyde). Nucleus of cells were counterstained using DAPI, and the cells were observed using ECLIPSE TE2000-U microscope.

Figure 21:
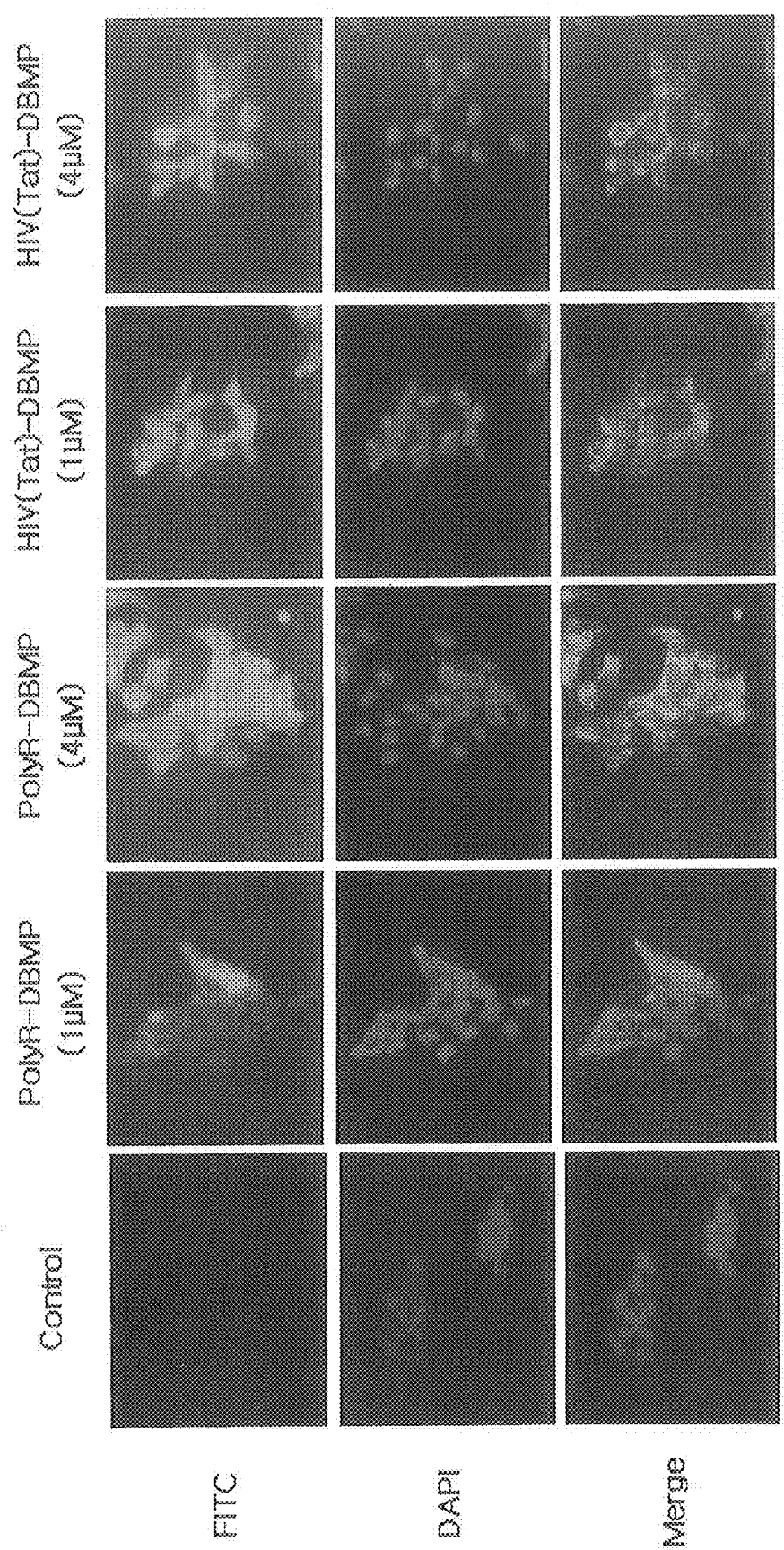
FIG. 21 is a fluorescence photograph showing PTD-conjugated DMBP peptides successfully introduced into the HEK 293 cell.

FIG. 21 shows that green fluorescence was detected in nucleus and cytosol of most cells, which reveals that PTD-DBMP were successfully introduced into the cells.

To investigate the effect of PTD-DBMP in the cells, HEK293 cells were incubated with 1 μM or 4 μM PTD-DBMP for 12 hours, and then the cell lysates were subjected into immunoblotting using anti-β-catenin, and anti-α-tubulin antibodies.

Figure 22:
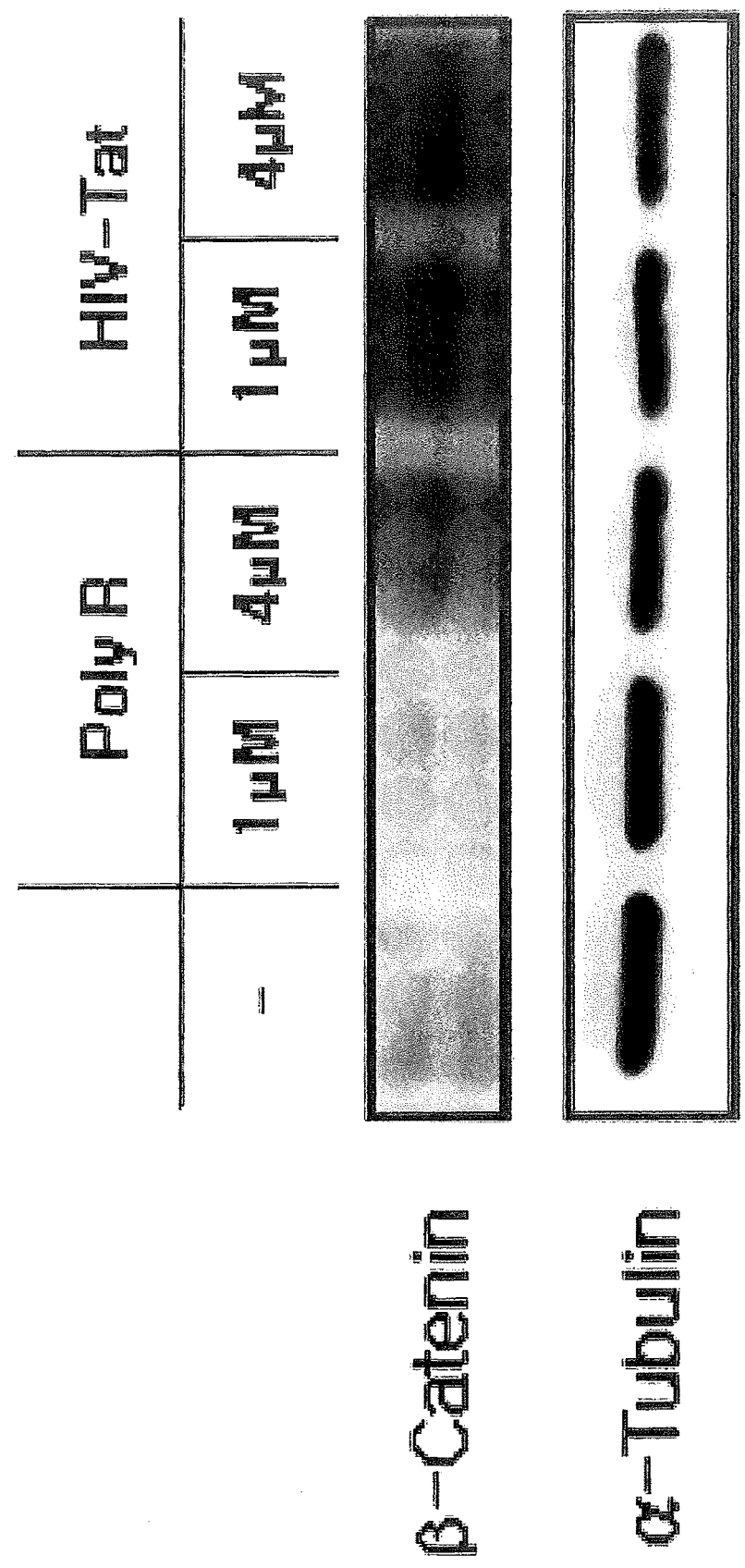
FIG. 22 shows the immunoblotting results showing a Wnt/β-catenin signaling pathway activated by introduction of the PTD-conjugated DBMP peptides into the HEK293 cell.

FIG. 22 shows that the amount of β-catenin increased in PTD-DBMP treated cells. This result shows that PTD-DBMP binds to Dvl-1 in competitive manner with Idbf, and it results in the activation of Wnt/β-catenin signaling (FIG. 22).

Figure 23:
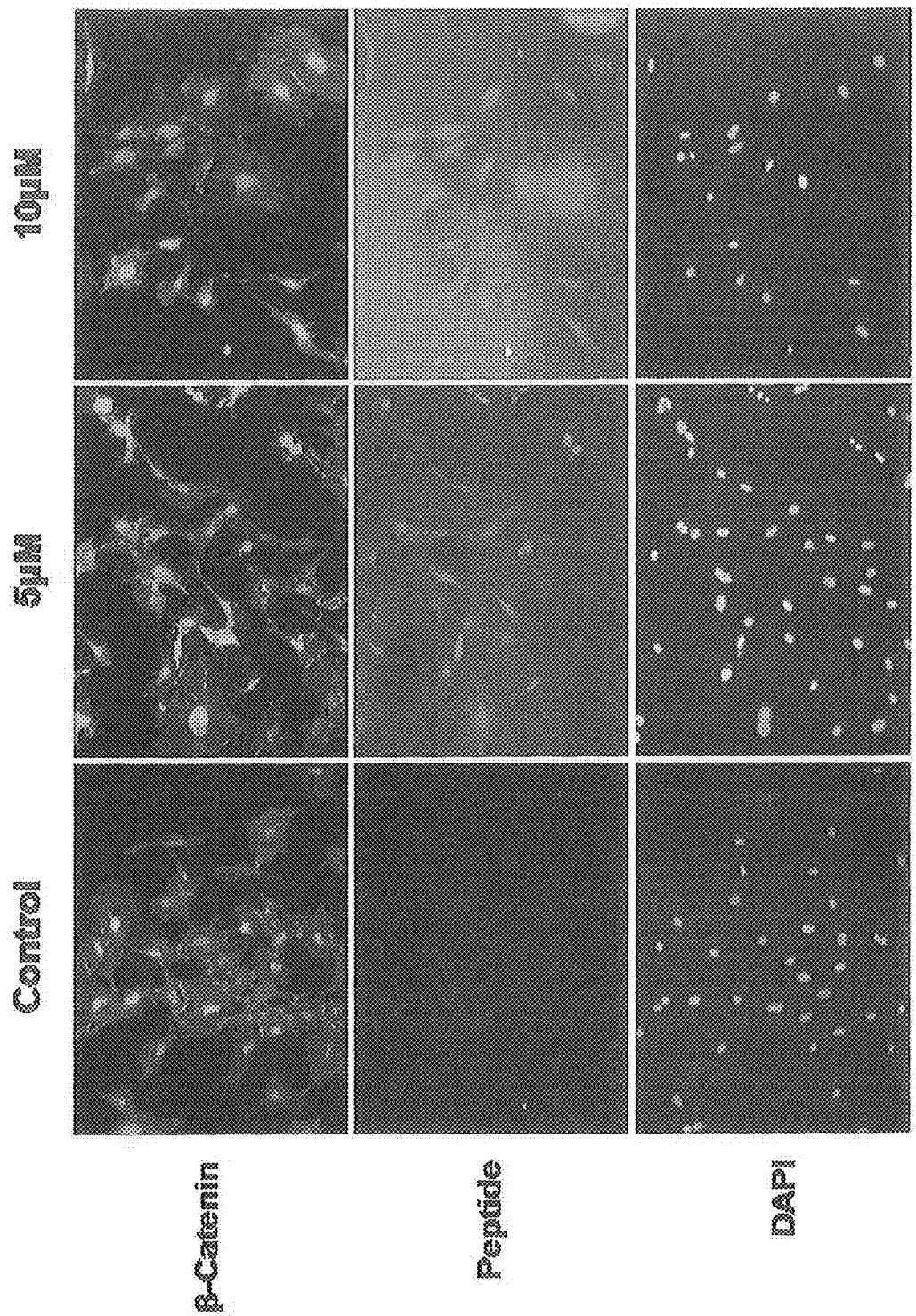
FIG. 23 shows the immunofluorescent staining results showing β-catenin in nuclei increased by introduction of the PTD-conjugated DBMP peptides into osteoblast (MC3T3E1).
Figure 24:
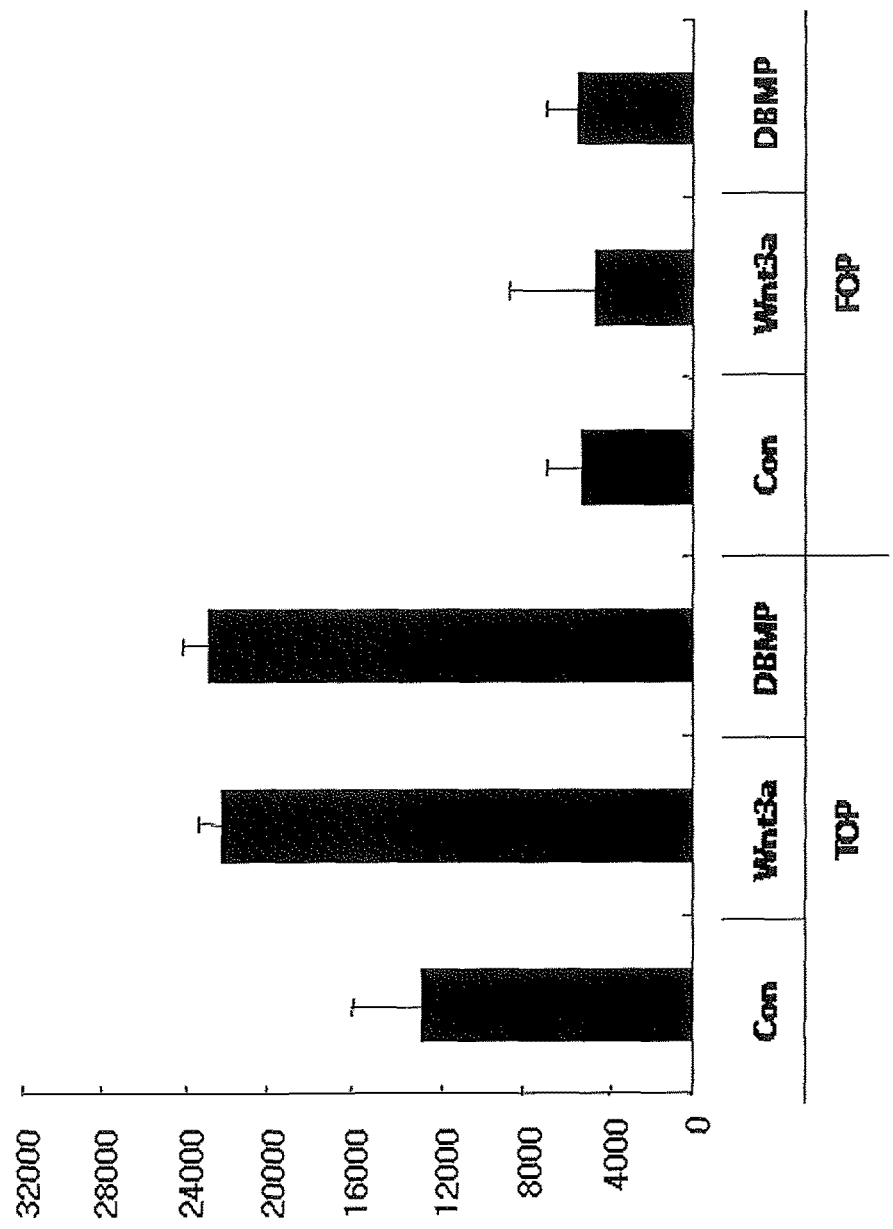
FIG. 24 shows the reporter assay results showing activities of the Wnt/β-catenin signaling pathway in osteoblast induced by treatment with the PTD-conjugated DBMP peptides.

8. Introduction of PTD-DBMP into Pre-Osteoblast (MC3T3E1) and the Effect of PTD-DBMP on Wnt/β-Catenin Pathway PTD-DBMP (SEQ ID NO: 26) was treated into MC3T3E1 cells, and then the introduction and effect of PTD-DBMP were monitored by immunocytochemistry analyses. MC3T3E1 cells were incubated on gelatin-coated glasses for 1 day, and then 5 μM or 10 μM PTD-DBMP were treated on the incubated cells for 12 hours. The PTD-DBMP-treated cells were washed with PBS, and then fixed using a fixative solution (99% methanol and 1% formaldehyde). The fixed cells were permeabilized with 0.2% saponin solution, and then incubated with anti-β-catenin antibody (home-made; 1:100). The cells were incubated with Alexafluor 488 conjugated secondary antibody, and then the nucleus of cells were counterstained with DAPI. Green fluorescence by FITC was observed on nucleus and cytosol of cells, which shows that PTD-DBMP was successfully introduced into the cells (FIG. 23). The activation of Wnt/β-catenin pathway in PTD-DBMP-treated MC3T3E1 cells were observed, which is evidenced by accumulation of β-catenin (red) in nucleus of the cells (FIG. 23), To investigate the effect of PTD-DBMP treatment on Wnt/β-catenin pathway of MC3T3E1 cells, 0.5 μg of pTOPFLASH or pFOPFLASH with 50 ng of pCMV-β-Gal was transfected into the cells. After 12 hours, the transfected cells were treated with 100 ng/ml Wnt3a, or 5 μM PTD-DBMP, and then incubated for 12 hours. Then the cells were washed with PBS, and then lysed in Lysis Buffer (Promega). The cell lysates were mixed with Luciferase Substrate (Promega) to monitor the luciferase activities. The luciferase activities were normalized by β-galactosidase activity, which shows transfection efficiency. Error bars in FIG. 24 indicates standard deviations of three independent experimental results, FIG. 24 shows that the activation of Wnt/β-catenin pathway by PTD-DBMP treatment is as significant as the activation by Wnt3a treatment.

Figure 25:
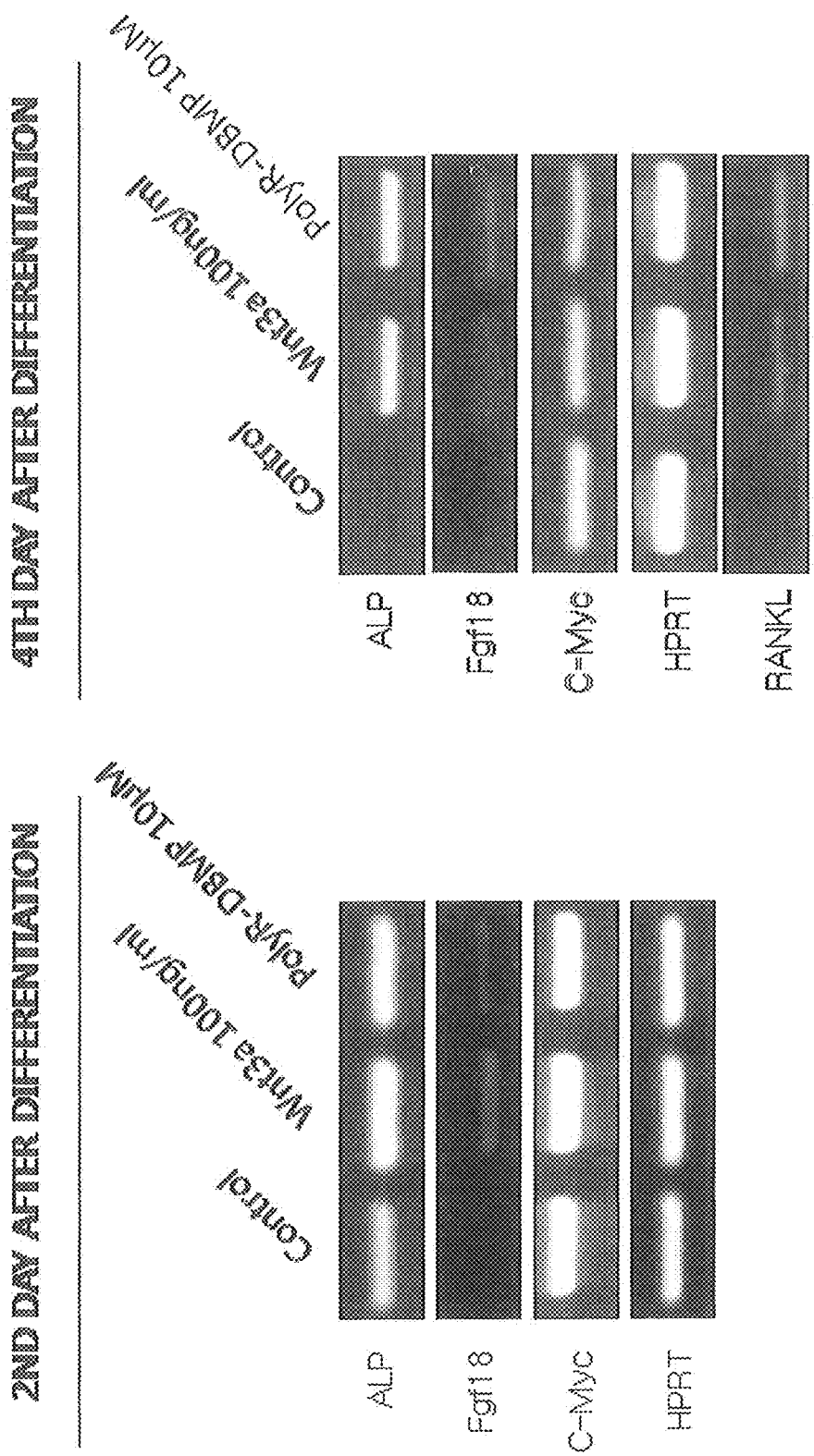
FIG. 25 shows the reverse transcriptase (RT)-PCR results showing differentiation of osteoblast induced by treatment with the PTD-conjugated DBMP peptides.

To study the effect of PTD-DBMP on osteoblast differentiation, 100 ng/ml Wnt3a, or 10 μM PTD-DBMP was treated on MC3T3E1 cells. The cells were harvested after 2, and 4 days later, and then subjected into RT-PCR to monitor the amounts of ALP, Fgf18, RANKL, and HPRT mRNAs. The mRNA amounts of osteoblast differentiation markers (ALP, Fgf18, RANKL) were increased by PTD-DBMP treatment, as well as by Wnt3a treatment (FIG. 25).

The invention claimed is:

1. A method of treating a disease or condition by blocking the binding of inhibitor of dishevelled and bone formation (Idbf) to dishevelled (Dvl), thereby activating signal transduction carried out through the Wnt/β-catenin signaling pathway, comprising administering an effective amount of an Idbf inhibitor to a subject in need thereof, wherein the Idbf inhibitor is a polypeptide consisting of the amino acid sequence set forth in SEQ ID NO: 4 (RKTGHQICKFRKC) or a conjugate of SEQ ID NO: 4 with a protein transduction domain (PTD) of 8-20 amino acids; and wherein the disease or condition is osteoporosis, insufficient bone growth, bone fracture, or insufficient bone density.

2. The method according to claim 1, wherein the polypeptide consists of the amino acid sequence set forth in SEQ ID NO: 4 and is further conjugated to a PTD of 8-20 amino acids.

3. The method according to claim 2, wherein the PTD is RRRRRRRR (SEQ ID NO: 28) or HIV-Tat (YGRKKRRQRRR) (SEQ ID NO: 29).

4. The method according to claim 2, wherein the polypeptide conjugated to a PTD consists of the amino acid sequence as set forth in SEQ ID NO: 26 or SEQ ID NO: 27.

* * * * *